(12) United States Patent
Verzal et al.

(10) Patent No.: US 12,311,179 B2
(45) Date of Patent: May 27, 2025

(54) IMPLANT-ACCESS INCISION AND SENSING FOR SLEEP DISORDERED BREATHING (SDB) CARE

(71) Applicant: INSPIRE MEDICAL SYSTEMS, INC., Golden Valley, MN (US)

(72) Inventors: Kevin Verzal, Lino Lakes, MN (US); John Rondoni, Plymouth, MN (US); David Dieken, Minneapolis, MN (US); Luke Lozier, Shorewood, WI (US); Darrell Wagner, Ham Lake, MN (US)

(73) Assignee: INSPIRE MEDICAL SYSTEMS, INC., Golden Valley, MN (US)

( * ) Notice: Subject to any disclaimer, the term of this patent is extended or adjusted under 35 U.S.C. 154(b) by 768 days.

(21) Appl. No.: 16/977,677

(22) PCT Filed: Feb. 4, 2020

(86) PCT No.: PCT/US2020/016533
§ 371 (c)(1),
(2) Date: Sep. 2, 2020

(87) PCT Pub. No.: WO2020/163292
PCT Pub. Date: Aug. 13, 2020

(65) Prior Publication Data
US 2020/0391028 A1    Dec. 17, 2020

Related U.S. Application Data

(60) Provisional application No. 62/801,219, filed on Feb. 5, 2019.

(51) Int. Cl.
*A61N 1/36* (2006.01)
*A61N 1/372* (2006.01)

(52) U.S. Cl.
CPC ........ *A61N 1/3611* (2013.01); *A61N 1/36139* (2013.01); *A61N 1/37205* (2013.01)

(58) Field of Classification Search
CPC .............. A61N 1/3611; A61N 1/36139; A61N 1/37205
USPC .......................................................... 607/42
See application file for complete search history.

(56) References Cited

U.S. PATENT DOCUMENTS

| 5,154,180 | A  | 10/1992 | Blanchet et al. |
| 5,335,657 | A  | 8/1994  | Terry et al. |
| 6,574,507 | B1 | 6/2003  | Bonnet |
| 6,587,725 | B1 | 7/2003  | Durand et al. |
| 6,773,404 | B2 | 8/2004  | Poezevera et al. |

(Continued)

FOREIGN PATENT DOCUMENTS

| EP | 2667933 A2    | 12/2013 |
| JP | 2007-502670 A | 2/2007  |

(Continued)

OTHER PUBLICATIONS

Blond, Benjamin N., Hirsch, Lawrence J., Chronic Ambulatory EEG With Implanted Electrodes, Neupsy Key, Jul. 9, 2018.

(Continued)

*Primary Examiner* — Ankit D Tejani
(74) *Attorney, Agent, or Firm* — Dicke, Billig & Czaja, PLLC

(57) ABSTRACT

A device and/or method to provide sleep disordered breathing (SDB) care includes an implant-access incision and/or a sensing element.

18 Claims, 18 Drawing Sheets

(56) References Cited

U.S. PATENT DOCUMENTS

| | | | |
|---|---|---|---|
| 7,190,995 | B2 | 3/2007 | Chervin et al. |
| 7,590,455 | B2 | 9/2009 | Heruth |
| 7,660,632 | B2 | 2/2010 | Kirby et al. |
| 7,717,848 | B2 | 5/2010 | Heruth et al. |
| 7,853,222 | B2 | 12/2010 | Buorget et al. |
| 7,854,767 | B2 | 12/2010 | May et al. |
| 7,865,244 | B2 | 1/2011 | Giftakis et al. |
| 7,945,316 | B2 | 5/2011 | Giftakis et al. |
| 7,957,809 | B2 | 6/2011 | Bourget et al. |
| 8,024,044 | B2 | 9/2011 | Kirby et al. |
| 8,055,348 | B2 | 11/2011 | Heruth et al. |
| 8,209,019 | B2 | 6/2012 | Giftakis et al. |
| 8,512,221 | B2 | 8/2013 | Kaplan et al. |
| 8,740,808 | B2 | 6/2014 | Curti et al. |
| 8,781,575 | B2 | 7/2014 | de Vos et al. |
| 9,889,299 | B2 | 2/2018 | Ni et al. |
| 2004/0015204 | A1 | 1/2004 | Whitehurst et al. |
| 2005/0042589 | A1 | 2/2005 | Hatlestad et al. |
| 2005/0081847 | A1 | 4/2005 | Lee et al. |
| 2005/0085874 | A1* | 4/2005 | Davis ............... A61N 1/37205 607/66 |
| 2006/0041277 | A1 | 2/2006 | Deem et al. |
| 2007/0255333 | A1 | 11/2007 | Giftakis et al. |
| 2008/0127978 | A1* | 6/2008 | Rubin ............... A61M 16/026 128/204.23 |
| 2009/0192556 | A1 | 7/2009 | Wu et al. |
| 2011/0202119 | A1* | 8/2011 | Ni ............... A61B 5/686 607/116 |
| 2011/0264164 | A1 | 10/2011 | Christopherson et al. |
| 2012/0089153 | A1 | 4/2012 | Christopherson et al. |
| 2012/0253249 | A1* | 10/2012 | Wilson ............... A61N 1/3611 607/42 |
| 2013/0231726 | A1 | 9/2013 | Johnson et al. |
| 2014/0076318 | A1 | 3/2014 | Flower et al. |
| 2015/0039046 | A1* | 2/2015 | Gross ............... A61N 1/3756 607/42 |
| 2015/0224018 | A1 | 8/2015 | Graindorge et al. |
| 2015/0224307 | A1* | 8/2015 | Bolea ............... A61N 1/36057 607/42 |
| 2015/0306391 | A1 | 10/2015 | Wu et al. |
| 2018/0116863 | A1 | 5/2018 | Shah et al. |
| 2018/0117316 | A1 | 5/2018 | Wagner et al. |
| 2018/0221660 | A1 | 8/2018 | Suri et al. |
| 2019/0029587 | A1 | 1/2019 | Walker et al. |
| 2019/0175026 | A1 | 6/2019 | Verzal et al. |
| 2020/0030609 | A9 | 1/2020 | Ni et al. |
| 2023/0095780 | A1 | 3/2023 | Rondoni et al. |

FOREIGN PATENT DOCUMENTS

| | | |
|---|---|---|
| JP | 2010-512831 A | 4/2010 |
| JP | 2011-522618 A | 8/2011 |
| JP | 2012-504467 A | 2/2012 |
| JP | 2015-533580 A | 11/2015 |
| WO | 2008072948 A1 | 6/2008 |
| WO | 2009149336 A1 | 12/2009 |
| WO | 2010039853 A1 | 4/2010 |
| WO | 201466666 A1 | 5/2014 |
| WO | 2017087681 A1 | 5/2017 |
| WO | 2017184753 A1 | 10/2017 |

OTHER PUBLICATIONS

Chervin, Ronald D., Malhotra, Raman K.; Burns, Joseph W., Respiratory Cycle-Related EEG Changes during Sleep Reflect Esophageal Pressures, 2008,Sleep 31(12):1713.

Chervin, Ronald D., Shelgikar, Anita V,; Jburns, Joseph W., Respiratory Cycle-Related EEG Changes: Response to CPAP, 2012, Sleep 35(2), pp. 203-209.

Ebben Matthew R., Sethi Nitin K., Conte Mary, Pollak Charles P., Labar Douglas, Vagus nerve stimulation, sleep apnea, and cpap titration, 2008, J Clin Sleep Med, 4(5), pp. 471-473.

Kaplan, Richard F., Wang, Ying, Loparo Kenneth A., Kelly Monica R., Bootzin Richard R., Performance evaluation of an automated singlechannel sleep-wake detection algorithm, Oct. 15, 2014, Nature and Science of Sleep, Oct. 15, 2014, pp. 113-122.

Motamedi-Fakhr, S., Moshrefi-Torbati, M., Hill, C.M., Paul, A. and Hill, M. (2010) On respiratory cycle related EEG changes (RCREC). At Congress of the International Pediatric Sleep Association joint meeting with Pediatric Sleep Medicine Conference Congress of the International Pediatric Sleep Association joint meeting with Pediatric Sleep Medicine, Presented Dec. 3, 2010.

O'Malley Edward B., Norman Robert G., Farkas Daniel et al. The addition of frontal EEG leads improves detection pf cortical arousal following obstructive respiratory events. Sleep 2003;26(4): p. 435.

Pillai, Ajay, Frederique Pierre, Ramachandran Siva K. et al., Correlation of Electroencephalographic Cortical Arousals In Sleep Studies With Excessive Daytime Sleepiness Scores, Oct. 2004, Chest, 125(4_Meeting Abstracts) 786S, doi:10:1378.

Pittson, DJ, Stradling JR, Autonomic markers of arousal during sleep in patients undergoing investigation for obstructive sleep apnoea, their relationship to EEG arousals, respiratory events and subjective sleepiness; 1998, J. Sleep Res. 7, pp. 53-59.

Penzel, Thomas, Kantelhardt, Jan W., Grote Ludger, Peter Jorg-Hermann, Bunde Armin, Comparison of Detrended Fluctuation Analysis and Spectral Analysis for Heart Rate Variability in Sleep and Sleep Apnea, Oct. 2003, IEEE Transactions On Biomedical Engineering, vol. 50, No. 10, pp. 1143-1151.

Šušmáková, K. Human Sleep and Sleep EEG, 2004, Measurement Science Review, vol. 4, Section 2, pp. 59-74.

Wang, Ying, Loparo, Kenneth A., Kelly, Monica R., Kaplan, Richard F., Evaluation of an automated single-channel sleep staging algorithm, 2015, Nature and Science of Sleep 2015:7 pp. 101-111.

PCT International Search Report and Written Opinion, Int'l Appl. No. PCT/US2020/016533, mailed May 6, 2020, pp. 1-13.

Lachlan D. Barnes et al., Detection of sleep apnea from single-channel electroencephalogram (EEG) using an explainable convolutional neural network (CNN); PLOS ONE, Sep. 13, 2022, pp. 1-18.

Ethan I. Huang et al., Respiratory Arousals in Patients with Very Severe Obstructive Sleep Apnea and How They Change after a Non-Framework Surgery; Healthcare, 10, 902, May 13, 2022, pp. 1-9.

T. Sugi et al., Automatic EEG arousal detection for sleep apnea syndrome; ScienceDirect, vol. 4, Issue 4, Oct. 2009, pp. 329-337.

Hyewon Han et al., Classification and automatic scoring of arousal intensity during sleep stages using machine learning; Scientific Reports, vol. 14, Issue 1, Mar. 12, 2024, pp. 1-12.

* cited by examiner

3200 — ARRANGING THE FIRST ELEMENT TO SENSE EEG INFORMATION

FIG. 25

3220 — OPERATING THE SECOND ELEMENT, BASED ON THE SENSED EEG INFORMATION, TO STIMULATE AN UPPER AIRWAY PATENCY NERVE TO TREAT SLEEP DISORDERED BREATHING

FIG. 26

3240 — SENSING THE EEG INFORMATION TO DETERMINE SLEEP STATE INFORMATION AND DETERMINING SDB CARE INFORMATION BASED ON THE DETERMINED SLEEP STATE INFORMATION

FIG. 27

3260 — SENSING THE EEG INFORMATION TO DETERMINE RESPIRATORY INFORMATION AND DETERMINING SDB CARE INFORMATION BASED ON THE DETERMINED RESPIRATORY INFORMATION

| 3310 | IMPLANTING ELEMENTS OF A SDB CARE DEVICE SOLELY WITHIN A HEAD-AND-NECK REGION |

↓

| 3320 | SENSING, VIA A FIRST IMPLANTED ELECTRODE OF THE SDB CARE DEVICE, EEG INFORMATION INCLUDING AT LEAST SLEEP STATE INFORMATION |

↓

| 3340 | STIMULATING, VIA A SECOND IMPLANTED ELECTRODE OF THE SDB CARE DEVICE, AN UPPER AIRWAY PATENCY NERVE TO TREAT SLEEP DISORDERED BREATHING |

FIG. 29

| 3350 | PERFORMING THE STIMULATING IN A CLOSED-LOOP MANNER BASED ON THE SENSED EEG INFORMATION |

FIG. 30

| 3360 | ARRANGING THE SECOND ELECTRODE IN ASSOCIATION WITH A MICROSTIMULATOR OF THE SDB CARE DEVICE |

FIG. 31

IMPLANT-ACCESS INCISION AND SENSING FOR SLEEP DISORDERED BREATHING (SDB) CARE

CROSS REFERENCE TO RELATED APPLICATION

This Utility Patent Application claims priority under 35 U.S.C. §371 to International Application Serial No. PCT/US20/16533, filed Feb. 4, 2020, which claims the benefit of U.S Patent Provisional Application Ser. No. 62/801,219, filed Feb. 5, 2019, all of which are incorporated herein by reference.

A significant portion of the population suffers from various forms of sleep disordered breathing (SDB). In some patients, external breathing therapy devices and/or mere surgical interventions may fail to treat the sleep disordered breathing behavior.

BRIEF DESCRIPTION OF DRAWINGS

FIGS. 25-26 are each a diagram schematically representing an example method including sensing EEG information and stimulating a nerve.

FIGS. 27-28 are each a diagram schematically representing an example method including sensing EEG information and determining SDB care information.

FIG. 29 is a flow diagram schematically representing an example method including implanting elements in a head-and-neck region, sensing EEG information, and stimulating a nerve.

FIG. 30 is a block diagram schematically representing an example method including closed-loop stimulation.

FIG. 31 is a block diagram schematically representing an example method including arranging a second element as a microstimulator.

DETAILED DESCRIPTION

Figure 1:
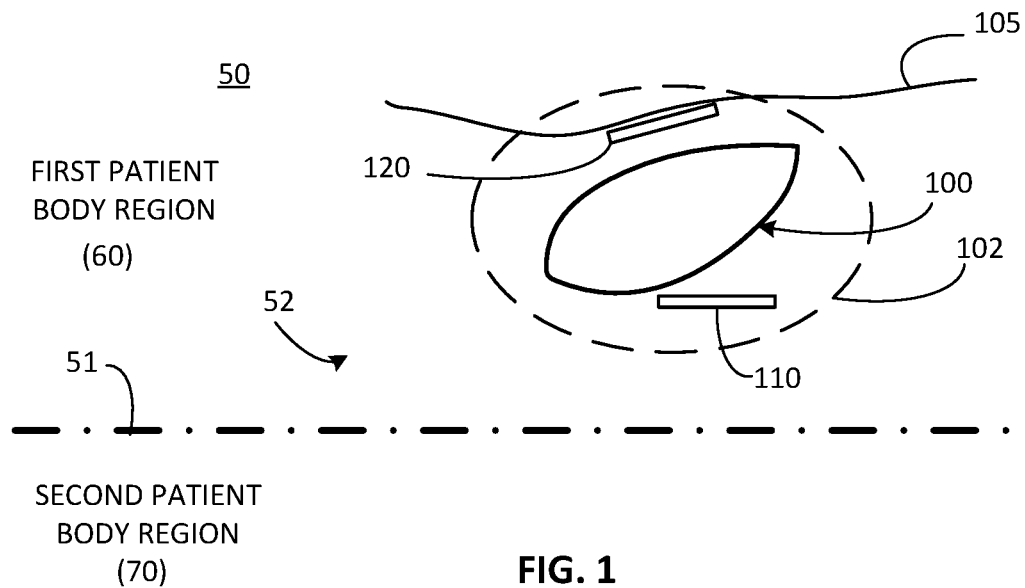
FIGS. 1 and 2 are each a diagram including a top view schematically representing an example device and/or example method including a first element and/or a second element implanted via a first implant-access incision in a first body region.

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure. The following detailed description, therefore, is not to be taken in a limiting sense. It is to be understood that features of the various examples described herein may be combined, in part or whole, with each other, unless specifically noted otherwise.

At least some examples of the present disclosure are directed to devices for diagnosis, therapy, and/or other care of medical conditions. At least some examples may comprise implantable devices and/or methods of implanting devices. At least some such examples comprise minimizing the number of incisions used to implant components and elements of such devices and/or in such methods. In some examples, multiple elements may be implanted via a single implant-access incision. In some examples, for a given method or device of care, the single implant-access incision comprises the sole implant-access incision to implement the care device and/or method of care.

At least some of the example devices and/or example methods may relate to sleep disordered breathing (SBD) care, which may comprise monitoring, diagnosis, and/or stimulation therapy. At least some examples may relate to cardiac care, drug delivery, and/or other forms of care, whether standing alone or in association with sleep disordered breathing (SDB) care.

In some examples, a method comprises chronically implanting, via a first implant-access incision in a first patient body region, at least a first element and a second element in the first patient body region. The method may comprise performing sensing, via the first element, first physiologic information in the first patient body region and/or may comprise operating the second element in the first patient body region. In some examples, the first element may comprise a sensing element or sensing device.

The particular operation of the second element may depend on the type of second element. For instances, in some examples the second element may comprise a stimulation electrode and thus, operating the second element comprises stimulating a tissue via the second element.

In some examples, the second element may comprise a monitoring device, such as monitoring cardiac conditions and/or other physiologic information or conditions. In such examples, operating the second element comprises monitoring such physiologic information or conditions. In some examples, the second element may comprise a drug delivery device, such as a pump, wherein operating the second element comprises delivering a drug and/or other substance within the patient's body.

In some examples, the first element and the second element may be combined into a single element or device.

At least some examples of the present disclosure comprise using central nervous system (CNS) information to inform and/or drive patient care. In some examples, the care may comprise sleep disordered breathing (SDB) care, which may comprise monitoring, diagnosis, and/or therapy, etc. with at least some therapy examples comprising stimulation of tissue to treat sleep disordered breathing (SDB). In some examples, the tissue may comprise an upper-airway-patency nerve and/or other tissue to maintain and/or restore upper airway patency.

In some examples, the CNS information may comprise electroencephalogram (EEG) information and/or other CNS-related information. In some examples, a sensing element used to sense EEG information is chronically implantable, such as in a subdermal location (e.g. subcutaneous location external to the cranium skull), rather than an intracranial position (e.g. interior to the cranium skull). In some examples, the EEG sensing element is placed and/or designed to sense EEG information without stimulating a vagus nerve at least because stimulating the vagal nerve may exacerbate sleep apnea, particularly with regard to obstructive sleep apnea. Similarly, the EEG sensing element may be used in a device in which a stimulation element delivers stimulation to a hypoglossal nerve or other upper airway patency nerve without stimulating the vagus nerve in order to avoid exacerbating the obstructive sleep apnea.

In some, the EEG sensing element is placed and/or designed to sense EEG information without causing (e.g. via stimulation) synchronization and/or without causing descynchronization of the EEG waveform(s).

In some examples in which a sensing element and a stimulation element may combined into a single element such as a stimulation electrode, the stimulation electrode may be chronically implanted in stimulating-relation to a nerve (e.g. upper airway patency nerve) in a position external to a patient's brain, and from which sensing of EEG information may be performed. In some such examples, the stimulation electrode may enable sensing EEG information and stimulation of the upper airway patency nerve. In some such examples, the combined sensing and stimulation element may obtain EEG information via single channel EEG sensing. In some such examples, the location of the stimulation electrode used for stimulation and sensing is positioned subdermally (e.g. under the scalp tissue) in the head-and-neck region, such as in a mandible-neck portion. In some examples, the mandible-neck portion of the final implant location of the stimulation electrode (also used for sensing) may sometimes be referred to as being a non-cranium final implant location. In some such examples of the stimulation electrode also acting as sensing element to sense EEG information, the method comprises arranging a final implant location of the stimulation electrode in a non-cranium location other than in the mandible-neck portion of the head-and-neck region. As further described later, in some examples the stimulation electrode (which combines a sensing element and a stimulation element) may comprise multiple electrodes while still acting as a single element for implantation purposes.

In some examples, the EEG sensing element(s) senses EEG information for sleep disordered breathing (SDB) information, such as but not limited to sleep state information and/or respiratory information. In some such examples, the EEG sensing element(s) senses the EEG-based respiratory information and/or EEG-based sleep state information, without using a torso-located respiratory sensor and/or without using a respiratory-dedicated sensor separate from the EEG sensing element. In some such examples, the EEG sensing element senses EEG information for sleep disordered breathing (SDB) information, such as but not limited to sleep state information and/or respiratory information, without using external respiratory sensing arrangements (e.g. nasal airflow and the like).

In some examples, the EEG sensing element senses EEG information for sleep disordered breathing (SDB) information, such as but not limited to sleep state information and/or respiratory information, without using an accelerometer. However, in some examples, an accelerometer may be used in association with sensed EEG information to sense, diagnose and/or treat sleep disordered breathing (SDB) behavior.

In some examples, the implantable device comprises a torso-free device in which no components are located in the patient' torso region. In some such examples, sensing elements, stimulation elements, power/control elements of the device are located solely in the head-and-neck region. In some such examples, the sensing elements, stimulation elements, power control elements are located within a predetermined distance of each other within a subcutaneous location and/or within a predetermined area of the subcutaneous location, thereby providing a small footprint for implantation. In some examples, a single element (which may combine sensing elements and stimulation elements) may be used to sense EEG and to stimulate an upper airway patency nerve (e.g. hypoglossal nerve).

These examples, and additional examples, are further described in association with at least FIGS. 1-31.

FIG. 1 is a diagram 50 schematically representing an example method 52 and/or device comprising chronic, subdermal implantation of at least a first element and/or a second element within a patient's body. In some examples, the implanted first and second elements may be used in a method (and/or device) to provide sleep disordered breathing (SDB) care, such as but not limited to, treating obstructive sleep apnea (OSA) via neurostimulation. As shown in FIG. 1, an example method comprises making a first implant-access incision 100 in a first patient body region 60, which may comprise any one of a variety of body regions, such as a torso region, head-and-neck region, leg region, arm region. In some examples, a first element 110 and a second element 120 are implanted via the first implant-access incision 100, and maneuvered within a subcutaneous area 102 in close proximity to the first implant-access incision 100. In some examples, the second element 120 is implanted to be coupled relative to a nerve 105. In some examples, the nerve 105 comprises an upper-airway-patency nerve, such as but not limited to a hypoglossal nerve. In such examples, the first patient body region 60 comprises a head-and-neck region. In some such examples, the second element 120 may comprise a stimulation element to deliver a stimulation signal to the nerve 105.

In some examples, the first element may form part of, and/or, be supported by a lead and the second element may form part of, and/or be supported by a lead. In some examples, the lead may comprise at least one elongate electrically conductive element (e.g. wires) extending within an electrically insulative cover and having electrically conductive opposite ends. At least some example leads for sensing and/or stimulation are shown later in at least FIGS. 9-16B.

In some examples, the example stimulation element(s) may comprise a cuff electrode comprising at least some of substantially the same features and attributes as described in Bonde et al. U.S. Pat. No. 8,340,785, SELF EXPANDING ELECTRODE CUFF, issued on Dec. 25, 2102 and Bonde et al. U.S. Pat. No. 9,227,053, SELF EXPANDING ELECTRODE CUFF, issued on Jan. 5, 2016, Johnson et al, U.S. Pat. No. 8,934,992, NERVE CUFF, issued on Jan. 13, 2015, and Rondoni et al, WO 2019/032890, CUFF ELECTRODE published on Feb. 14, 2019, each of which is hereby incorporated by reference in their entirety. Moreover, in some examples a stimulation lead, which may comprise one example implementation of a stimulation element, may comprise at least some of substantially the same features and attributes as the stimulation lead described in U.S. Pat. No. 6,572,543 to Christopherson et al., and which is incorporated herein by reference in its entirety.

It will be understood that in some examples, each given stimulation element may comprise an array of electrically conductive elements (e.g. electrodes, electrode contacts, etc.), which may be arranged in in a wide variety of configurations, such as but not limited to a row, rows, staggered configurations, grid (2×2, 3×3), and combinations thereof. In some such examples, these electrically conductive elements may be implemented as a cuff electrode as previously noted and/or as described later in association with at least FIGS. 17A-17C.

In some examples in which the first element and/or second element may be combined into a single element, this arrangement may be implemented according to the example cuff electrode 1220 as later described in association with at least FIGS. 17A-17C, in which at least some electrodes may be used solely for stimulation, at least some electrodes may be used solely for sensing, or some electrodes may be used for both stimulation and sensing subject to timing and/or other usage parameters.

In some examples, when various examples within the present disclosure refer to a stimulation element as comprising a stimulation electrode, it will be understood that the stimulation electrode may comprise a single electrode or multiple electrodes.

In some such examples as noted above, the sensing element may form part of the sensing lead and/or the stimulation element may form part of the stimulation lead. FIGS. 9-17C provide at least some illustrative examples of such sensing leads and/or stimulation leads. It will further understood that in at least some of the examples shown in FIGS. 1-5, and the following examples in FIGS. 6-17C, such leads (to support or incorporate a sensing element and/or stimulation element) may not be shown for illustrative simplicity.

As shown in FIG. 1, the dashed line 51 schematically identifies a border or transition between first patient body region 60 and second patient body region 70 with it being understood that dashed line 51 does not necessarily correspond to a physically identifiable feature on a patient's body.

In some examples, the first element 110 may be used to sense physiologic information within the first patient body region 60 (e.g. head-and-neck region). The sensed physiologic information may be indicative of a physiologic information or condition within the first patient body region 60 and/or within the second patient body region 70 (e.g. a torso region).

In some examples, at least some of the information sensed via first element 110 may comprise information sensed and/or tracked via example care engine 2500, as later described and illustrated in association with FIG. 18.

In some examples, the second element 120 also may be used to sense physiologic information within the first patient body region 60 (e.g. head-and-neck region). The sensed physiologic information may be indicative of a physiologic information or condition within the first patient body region 60 and/or within the second patient body region 70. In some such examples, the second element 120 may be combined with the first element 110 into a single element. In some such examples, the combined first and second element may comprise a stimulation electrode in stimulating-relation to a nerve (e.g. upper airway patency nerve) in a position external to a patient's brain, and from which sensing of EEG information may be performed. In some such examples, the stimulation electrode may be located in a mandible-neck area (of a head-and-neck region) and the same electrode(s) may be used to sense EEG information. In some examples, the combined sensing and stimulation element may obtain EEG information via single channel EEG sensing. In some examples, the combined sensing and stimulation element may be implemented according to one of the example implementations as described later in association with at least FIGS. 17A-17C.

Figure 2:
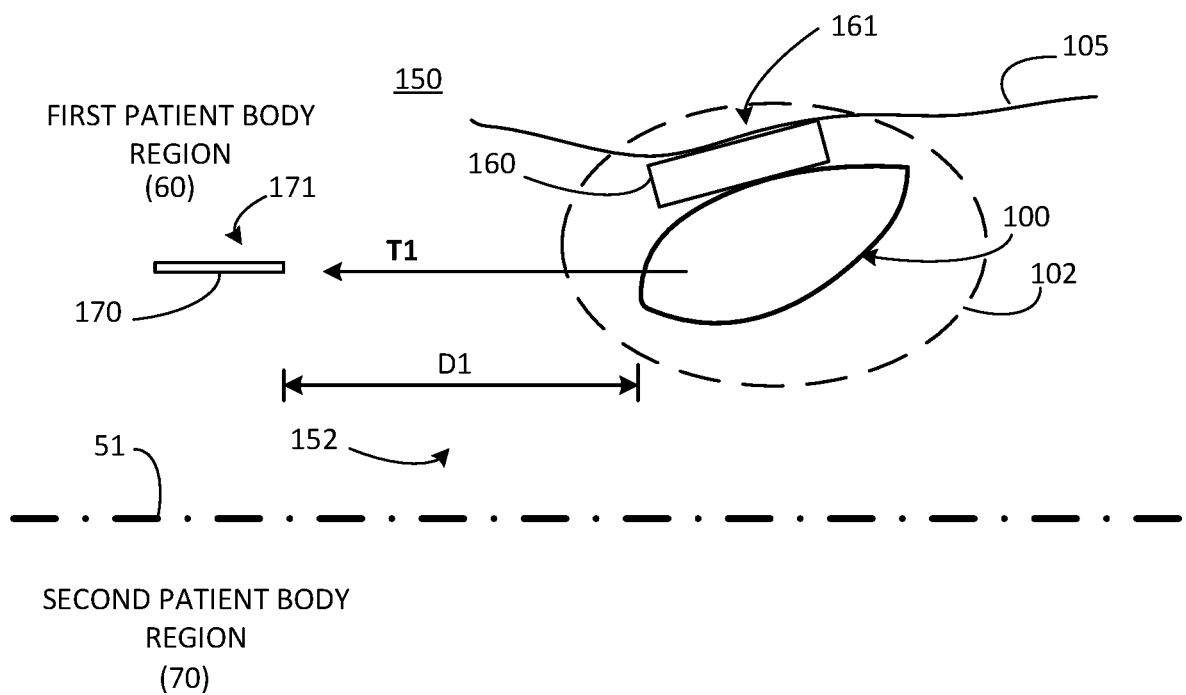

FIG. 2 is a diagram 150 schematically representing an example method 152 and/or device comprising implantation of at least a first element and/or a second element within a patient's body. In some examples, method 152 may comprise at least some of substantially the same features and attributes as method 52, except with first element 170 being implanted subcutaneously some distance (D1) from the first implant-access incision 100 after being introduced into the first patient body region 60 via the first implant-access incision 100 and then tunneled (directional arrow T1) to its desired location. In such examples, the tunnel or path is created via subcutaneously advancing a tunneling rod or similar instruments from the first implant-access incision 100 to the final implant location of the first element 170. In some examples, the distance (D1) may be representative of a length of the tunnel and/or a length of the tunnel rod (or other instrument) used to form the tunnel. In some examples, the distance D1 corresponds a distance from the implant-access incision to the target area at which sensing of physiologic information is to be performed via first element 170. In some examples, the distance D1 may have a minimum value which is at least or more than a first multiple of a length (or greatest dimension) of the first element 170 (e.g. sensing element). In some examples, the first multiple may be at least three, i.e. 3 times the length (or greatest dimension) of the first element 170. In some examples, the distance D1 may have a maximum value which is the same as or less than a second multiple of the length (or greatest dimension) of the first element 170. In some examples, the second multiple may be 10 times the length (or greatest dimension) of the first element 170.

In some examples, the first multiple associated with the minimum value (of distance D1) and the second multiple associated with the maximum value (of distance D1) may be a multiple of a length, width, area, or greatest dimension of first implant-access incision 100 instead of being a multiple of the length or greatest dimension of first element 170.

In some examples, the first multiple associated with the minimum value (of distance D1) and the second multiple associated with the maximum value (of distance D1) may be a multiple of a diameter of a lead (instead of being a multiple of the length or greatest dimension of first element 170). The lead may support first element 170, with the lead extending from at least the first implant-access incision 100 to the final implant location of the first element 170. In some such examples, the first multiple (minimum value) may be 5 times a diameter of the lead while in some such examples, the second multiple (maximum value) may be 10 times a diameter of the lead.

In some instances, the above-described distance relationships between the final implant location 171 of the first element 170 and the first implant-access incision 100 may sometimes be referred as the first element 170 (e.g. a sensing element) being located remotely from the first implant-access incision 100.

To the extent that the first element 170 is located remotely from, and placed into its final implant location 171 via, an implant-access incision used to place the second element 160 in a final implant location 161 in close proximity (i.e. not remote) to the implant-access incision, then the first element 170 may sometimes be referred to as being an incision-less or incision-free implant location because the first element 170 was not placed via its own implant-access incision, but instead the implant-access incision (e.g. 100) used primarily to place second element 160 (in its final implant location 161) was used to introduce, advance, place the first element 170 in its final implant location 171.

As in FIG. 1, the first element 170 may comprise a sensing element in some examples.

In some examples, the second element 160 may comprise a stimulation element, such as second element 120 (FIG. 1), or may comprise a microstimulator to stimulate nerve 105. In either case, the second element 160 is introduced into its subcutaneous location via first implant-access incision 100. Via the arrangement in FIG. 2, the first element 170 may be implanted in a subcutaneous location without employing a separate implant-access incision at the target location for the first element 170. Rather, a single implant-access incision 100 is used to implant both the second element 160 and the first element 170 despite the spacing (e.g. D1) between their respective final implanted locations within the first patient body region 60.

In some examples, the first element 170 and the second element 160 may be electrically connected relative to a common element, such as implantable pulse generator (IPG) with such connective wires omitted for illustrative clarity or with such connection being wireless. In some instances, the example of connective wires may take the form of a separate lead for each element 170, 160. In some examples, such as when the second element 160 may comprise a microstimulator or other pulse generator, then the method and/or device may comprise a lead electrically and mechanically connecting the first element 170 to the second element 160. Of course, in some examples, the first element 170 and the second element 160 also may be in wireless communication with each other and/or with a common element such as an implantable pulse generator (IPG).

In some examples in which first element 170 comprises a sensing element which forms part of a lead, the lead may have a length generally corresponding to the distance D1 between the final implant location 171 of the first element 170 and the final implant location 161 of the second element 160.

In some such examples, the implantation of the first element 170 in FIG. 2 may sometimes be referred to as being an incision-less implantation because the first element 170 is placed into its final implant location 171 without having an implant-access incision at or in close proximity to the final implant location 171 of the first element 170. Some details regarding such incision-less implantation of the first element 170, such as a sensing element, are further described later in association with at least FIGS. 6, 8, and 13C. In some examples, at least some of substantially the same features and attributes of the examples associated with FIGS. 6, 8, and 13C may be implemented as part of implementing the example associated with FIG. 2.

Figure 3:
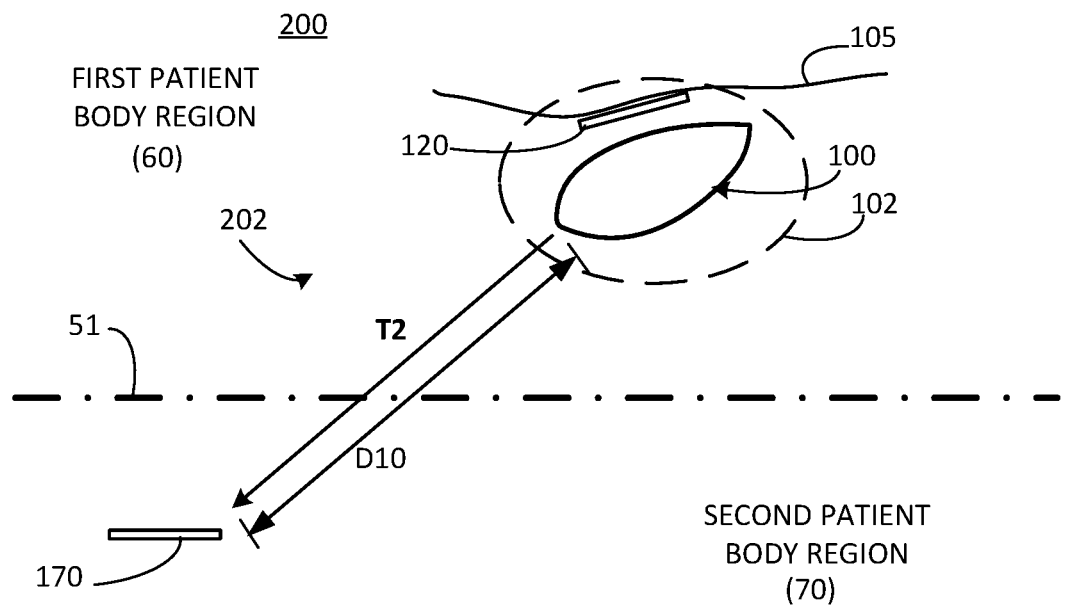
FIGS. 3 and 4 are each a diagram including a top view schematically representing an example device and/or example method including implanting, via a first implant-access incision in a first body region, at least a first element in the first body region and a second element in a second body region.

FIG. 3 is a diagram 200 schematically representing an example method 202 and/or device comprising implantation of at least a first element and/or a second element within a patient's body. In some examples, method 202 may comprise at least some of substantially the same features and attributes as method 152, except with first element 170 being implanted subcutaneously in a second patient body region 70 some distance D10 from the first implant-access incision 100 after being introduced into the first patient body region 60 via the first implant-access incision 100 and then tunneled (directional arrow T2) to its desired location. Via this arrangement, the first element 170 may be placed in its desired location without forming a separate implant-access incision at the target location of the first element 170 in the second patient body region 70. In some such examples, the first patient body region 60 comprises a head-and-neck region while the second patient body region 70 comprises a torso region, which may in turn comprise a pectoral region in some examples.

Figure 4:
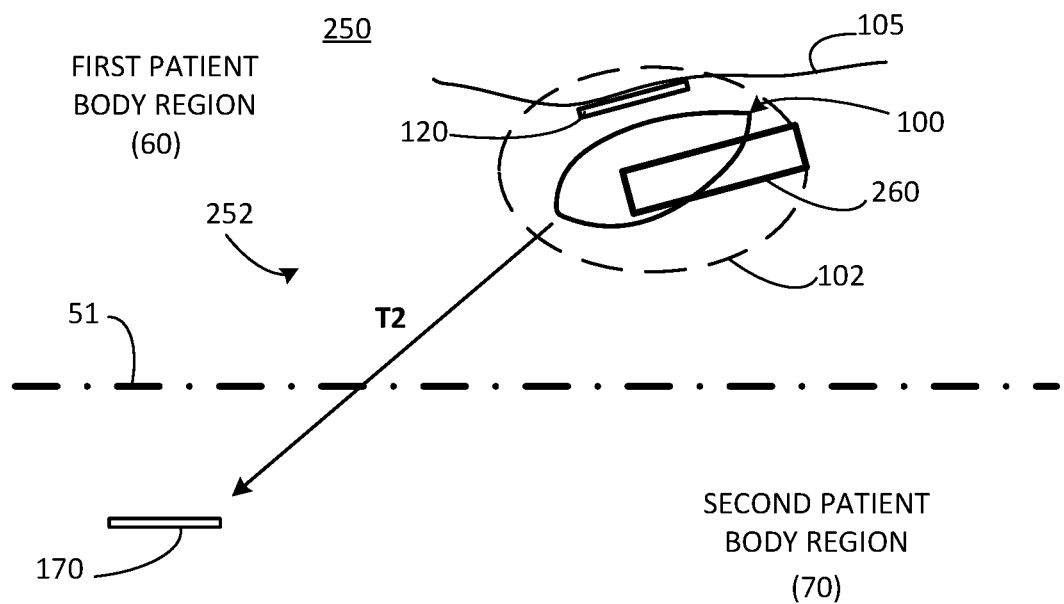

FIG. 4 is a diagram 250 schematically representing an example method 252 and/or device comprising implantation of at least a first element and a second element within a patient's body. In some examples, device and/or method 252 may comprise at least some of substantially the same features and attributes as method 202, except further comprising implanting a microstimulator 260 via the first implant-access incision 100 to be in electrical communication with the second element 120 to stimulate nerve 105. Although FIG. 4 depicts microstimulator 260 in the general vicinity of nerve 105 and of the second element 120 for illustrative simplicity, it will be understood that in some examples the microstimulator 260 may be positioned to directly engage nerve 105, and the microstimulator 260 may be combined with the second element 120 or replace the second element 120. In some examples, the microstimulator 260 may sometimes be referred as a power/control element.

In some example implementations of the present disclosure, a microstimulator may comprise at least some of substantially the same features and attributes as the example microstimulators and related elements as described and illustrated in PCT Application PCT/US2016/062546, titled MICROSTIMULATION SLEEP DISORDERED BREATHING (SDB) THERAPY DEVICE, and published as WO 2017/087681 on May 26, 2017, (and which has been filed as a U.S. National Stage application Ser. No. 15/774, 471), and which is incorporated by reference herein in its entirety.

Figure 5:
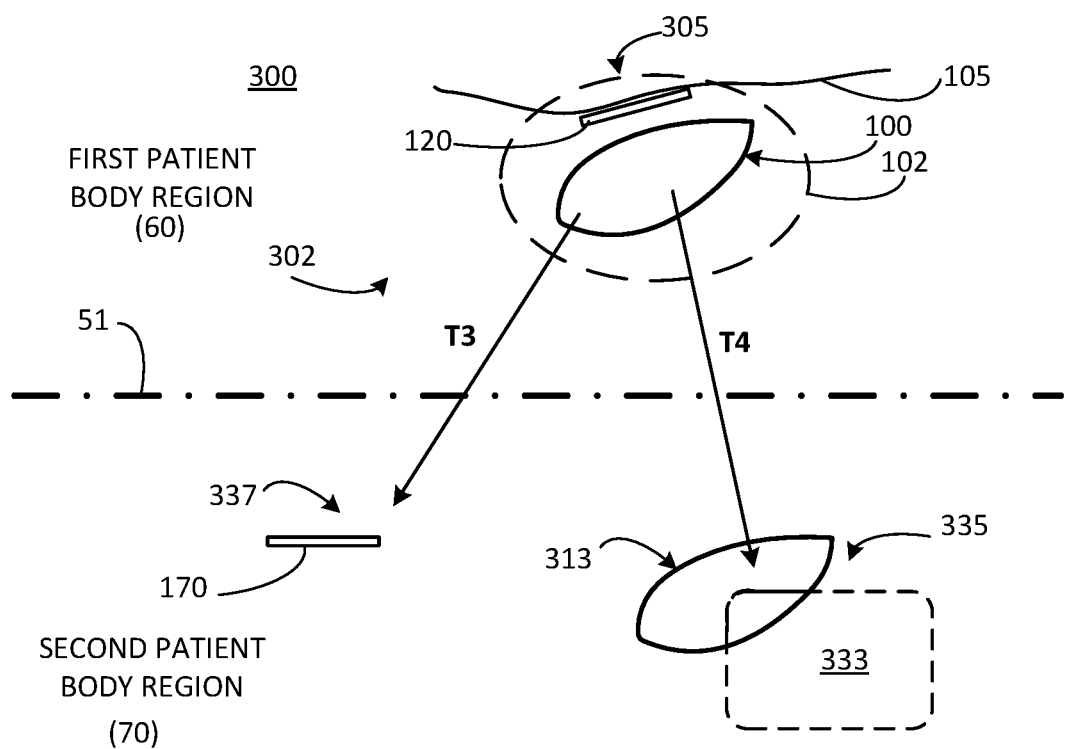
FIG. 5 is a diagram including a top view schematically representing an example device and/or example method including implanting, via a first implant-access incision in the first body region, at least a first element in a first body region and a second element in the second body region and implanting, via a second implant-access incision in the second body region, a power/control element in the second body region.

FIG. 5 is a diagram 300 schematically representing an example method 302 and/or device comprising implantation of at least a first element and a second element within a patient's body. In some examples, device and/or method 302 may comprise at least some of substantially the same features and attributes as method 202 in FIG. 3, except further comprising implanting a pulse generator 333, via a second implant-access incision 313, in the second patient body region 70. In some such examples, the second element 120 comprises a stimulation element which may be connected to the pulse generator 333 via a lead which may be tunneled (T4) from the first patient body region 60 to the second patient body region 70 to electrically connect the second element 120 to the pulse generator 333. However, instead of placing first element 170 via a third implant-access incision, the first element 170 is tunneled (T3) to its desired location from the first implant access incision 100 in order to reduce the number of implant access incisions made to implant the device 302 (e.g. to implement the method).

In some examples, the sensing element 170 and stimulation element 120 may be electrically and mechanically connected to a power/control element (e.g. pulse generator 333, microstimulator, etc.) via a lead, such as a sensing lead or stimulation lead. In some such examples, a stimulation lead including stimulation element 120 may be subcutaneously advanced between the implant-access incision 100 and implant-access incision 313, such as via a subcutaneous path or tunnel (e.g. T4).

Similarly, in some examples, a sensing lead including sensing element 170 may be subcutaneously advanced between the implant-access incision 100 and the above-described final implant location 337 of the sensing element 170, such as via a subcutaneous path or tunnel (e.g. T3).

As shown in FIG. 5, via method 302 the stimulation element 120 is placed into a final implant location 305 while the first element 170 is placed into a final implant location 337, and the power/control element 333 is placed into its final implant location 335.

However, with further reference to at least FIG. 5, in some examples, the stimulation element 120 may be in wireless electrical communication with the pulse generator 333 and/or the sensing element 170 may be in wireless electrical communication with the pulse generator 333. Moreover, in some examples, any one of the arrangements throughout FIGS. 1-17C may be implemented via such wireless electrical communication for sensing element(s) and/or stimulation element(s). In some of the examples involving wireless communication, the first element 170 may still be placed into its final implant location via an incision-less implantation method as described above.

Figure 6:
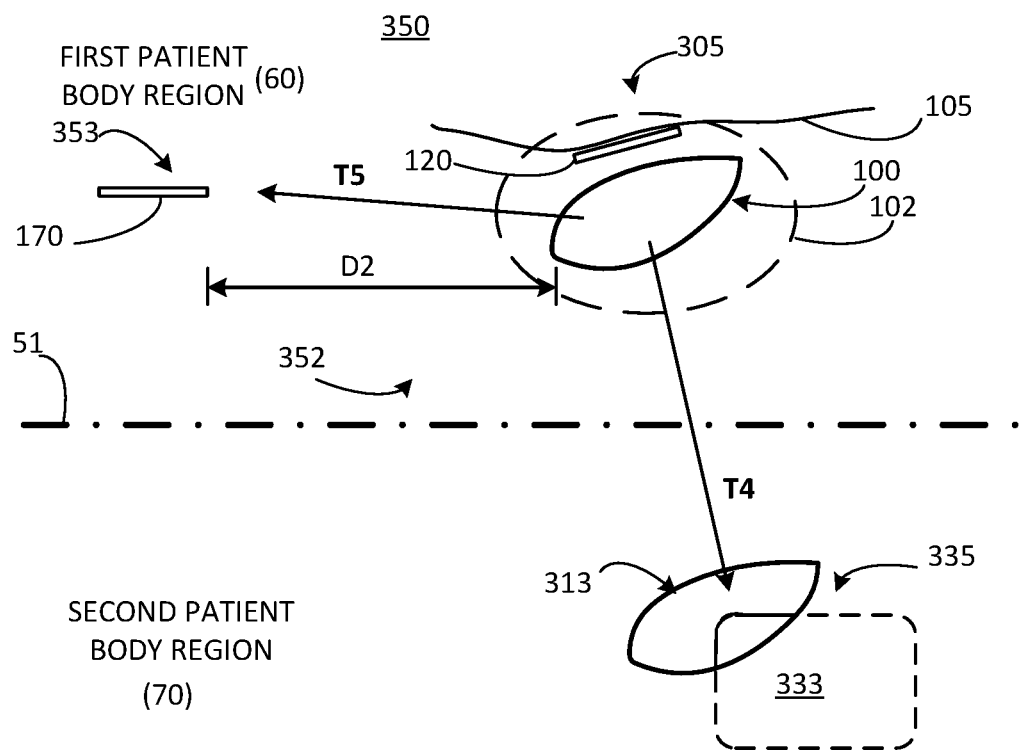
FIG. 6 is a diagram including a top view schematically representing an example device and/or example method including implanting, via a first implant-access incision in a first body region, both a first element and a second element in the first body region and implanting, via a second implant-access incision in a second body region, a power/control element in the second body region.

FIG. 6 is a diagram 350 schematically representing an example method 352 and/or device comprising implantation of at least a first element and a second element within a patient's body. In some examples, device and/or method 352 may comprise at least some of substantially the same features and attributes as method 302 in FIG. 5, except for implanting the first element 170 in the first patient body region 60 (instead of in the second patient body region 70) after introducing the first element 170 via the first implant access incision 100. Accordingly, in this example arrangement, both the first element 170 and the second element 120 are implanted in the first patient body region 60 via the first implant-access incision 100, and in some examples, a third element 333 (e.g. power/control element, a pulse generator, or monitor) is implanted in the second patient body region 70 via a second implant-access incision 313 located in the second patient body region 70. The first element 170 (e.g. for sensing) may be implanted via tunneling (T5) from the first implant-access incision 100 and a lead (which supports second element 120) between the second element 120 and the pulse generator 333 may be implanted via tunneling (T4) between the first implant-access incision 100 and the second implant-access incision 313, as previously described in association with at least FIG. 5.

As shown in FIG. 6, via method 352 the stimulation element 120 is placed via subdermal implantation into a final implant location 305 while the first element 170 is placed via subdermal implantation at implant-access incision 100 and tunneling (T5) into a final implant location 353, and the power/control element 333 is placed into its final implant location 335 via implant-access incision 313.

As further shown in FIG. 6, the first element 170 (e.g. sensing element) is spaced apart from implant-access incision 100 (and from second element 120) by a distance D2. In some examples, the distance D2 of separation between first element 170 and the implant-access incision 100 (and second element 120) according to the incision-less implantation of first element 170 (for placement at its final implant location) comprises at least some of substantially the same features and attributes as the distance (D1) relationships as previously described in association with FIG. 2.

Figure 7:
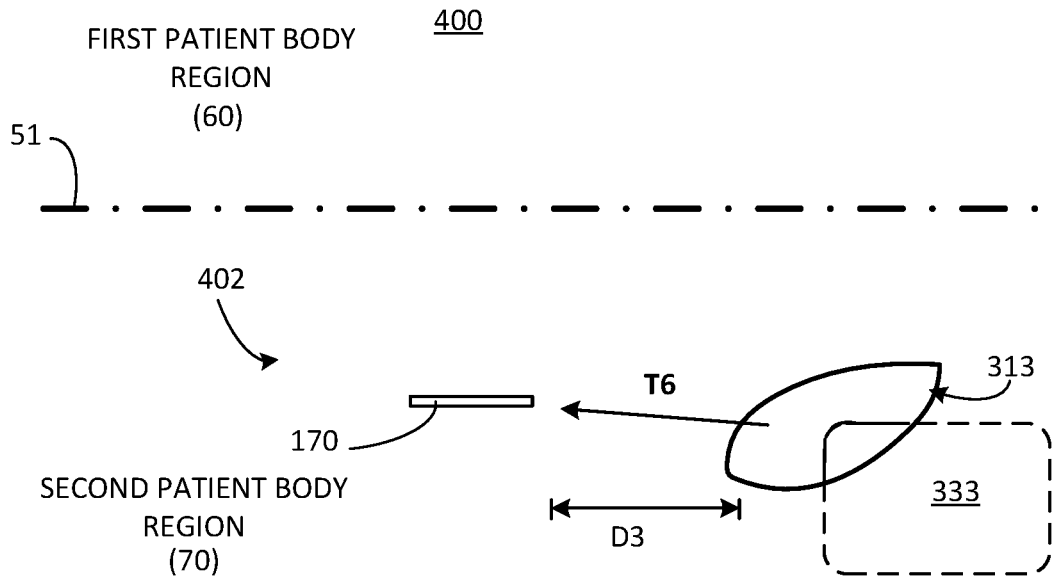
FIG. 7 is a diagram including a top view schematically representing an example device and/or example method including implanting, via a first implant-access incision in a second body region, both a second element and a power/control element in the second body region.

FIG. 7 is a diagram 400 schematically representing an example method 402 and/or device comprising implantation of at least a first element and a second element within a patient's body. As shown in FIG. 7, method 402 comprises implanting the first element 170 in the second patient body region 70 via an implant-access incision 313, which is located in the patient body region 70. The first element 170 is locatable in close proximity to the implant-access incision 313. However, in some examples like the previous examples in FIGS. 2-6, the first element 170 may be placed remoted (e.g. spaced apart by distance D3) from the implant-access incision 313 via tunneling (T6) subcutaneously to a target location. In some examples, the first element 170 comprises a sensing element.

In addition, method 402 comprises implanting a second element 333 into the second patient body region 70 via an implant-access incision 313, which is located in the second patient body region 70. In some such examples, the second element 333 may comprise a stimulation element, which may comprise a power/control element (e.g. pulse generator) in some examples. However, in some examples the second element 333 may comprise a monitoring device without a stimulation element.

Figure 8:
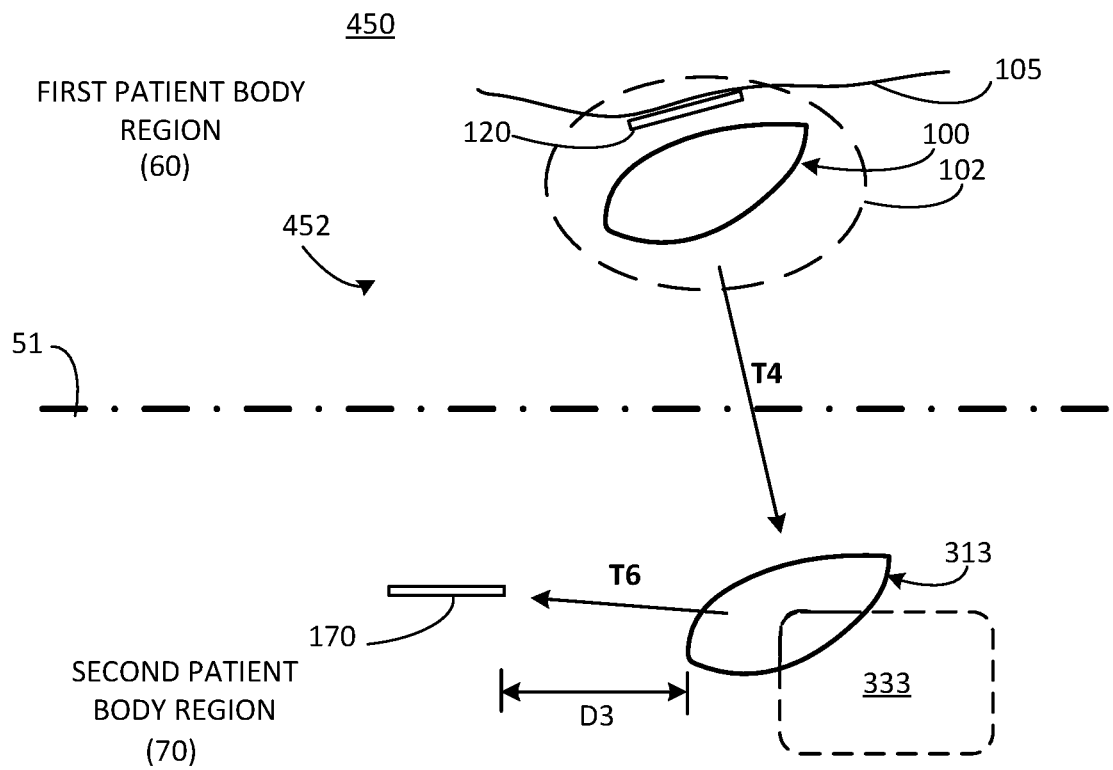
FIG. 8 is a diagram including a top view schematically representing an example device and/or example method including implanting, via a first implant-access incision in a second body region, both a second element and a power/control element in the second body region and implanting, via a second implant-access incision in a first body region, a first element.

FIG. 8 is a diagram 450 schematically representing an example method 402 and/or device comprising implantation of at least a first element and a second element within a patient's body. In some examples, device and/or method 452 may comprise at least some of substantially the same features and attributes as method 402 in FIG. 7, except for implanting a second element 120 in the first patient body region 60 via a first implant-access incision 100, which is located in the first patient body region 60. In some such examples, the second element 120 may be placed in stimulating-relation to a nerve 105 nearby the first implant-access incision 100 and arranged in electrical connection to the third element 333 via a lead tunneled (T4) subcutaneously from the first implant-access incision 100 (in the first patient body region 60) to the third element 333 near the second implant-access incision 313 (in the second patient body region 70). As noted elsewhere, in some such examples the electrical connection between the second element 120 and the third element 333 may be wireless, and the electrical connection between the first element 170 and the third element 333 may be wireless.

Via at least some of the example arrangements shown in FIGS. 1-8, a first element (e.g. 110, 170) may sense physiologic information (e.g. respiratory information) to determine patient information, such as sleep quality, episodes of sleep disordered breathing, respiratory information (e.g. inspiration, expiration, etc.), etc. In some such examples, at least some of the sensed information is used in a closed-loop manner to modulate stimulation of nerve 105 via second element (e.g. 120, 160) as controlled via third element (e.g. 333), with such modulation comprising at least one of initiating and/or terminating stimulation, as well as adjusting stimulation via at least one of increasing, maintaining, or decreasing intensity of the stimulation. In some examples, the intensity may be adjusted via modifying an amplitude, frequency, pulse width, etc. of the stimulation signal. In some such examples, as later described more fully in association with at least some example implementations, the sensed information may comprise information regarding sleep quality, sleep stage, and the like. In some such examples, this sensed information may be obtained as an EEG signal. In some examples, a lower stimulation level may be delivered in REM sleep stage than deeper sleep states. In some such examples, the sensed information may comprise respiratory information obtained from the sensed EEG information.

These, and additional features and attributes associated with FIGS. 1-8 will be further described in association with at least FIGS. 9-17C and at least FIGS. 18-31. Moreover, at least some of the examples described in association with FIGS. 9-31 may comprise example implementations of the examples described in association with FIGS. 1-8.

Moreover, at least some aspects of the example implementations of the arrangements in FIGS. 1-8 are further described and illustrated in association with at least FIGS. 9-17C in specific relation to the head-and-neck region as one example implementation of a first patient body region.

Figures 9, 10:
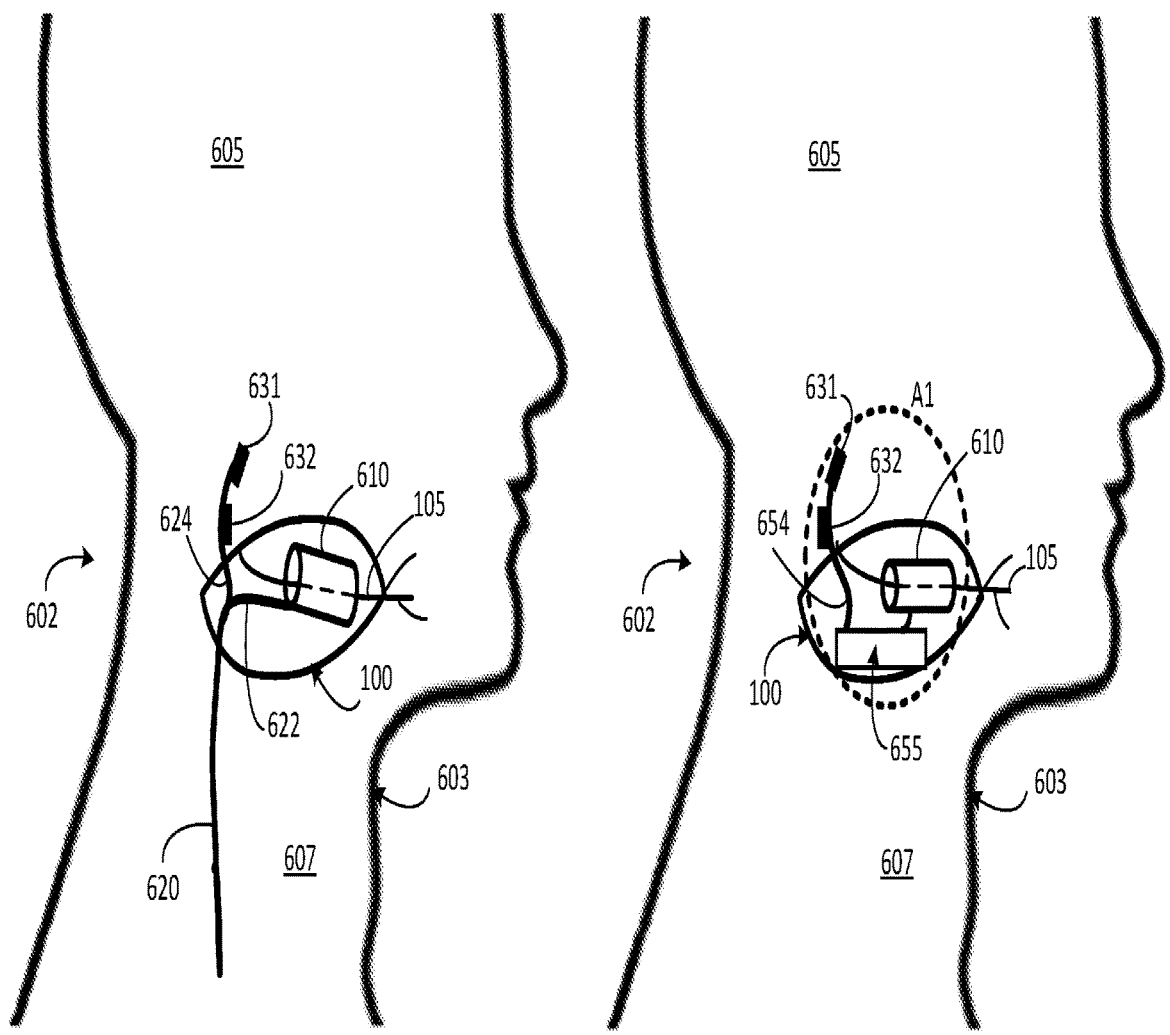
FIG. 9 is a diagram including a top view schematically representing an example device and/or example method including implanting, via a first implant-access incision in a first body region, both a stimulation element and sensing elements.
FIG. 10 is a diagram including a top view schematically representing an example device and/or example method including implanting, via a first implant-access incision in a first body region, a stimulation element, a power/control element, and sensing elements.

FIG. 9 is a diagram 600 schematically representing an example device and/or method 602 employed in at least a head-and-neck region 603 of a patient's body.

In some examples, a main lead 620 extends from a torso body region, such as one of the previously illustrated torso regions, as schematically represented in some examples by second patient body region 70 in FIGS. 1-8. At its proximal end, the main lead 620 is electrically connected to a sensor monitor and/or a pulse generator (such as IPG 333 in FIGS. 6-8). The lead 620 comprises first distal portion 622 and second distal portion 624, which are bifurcated from each other with first distal portion 622 supporting a stimulation element 610. In some examples, the stimulation element 610 may comprise a cuff electrode (as previously described in association with at least FIGS. 1-2 and/or with at least FIGS. 17A-17C), which is releasably securable to, and electrically connected relative to, nerve 105 or may comprise another type of electrode in stimulating-relation relative to nerve 105. In some examples regarding the device/method 602 in FIG. 9 and/or the later examples in FIGS. 10-16B, the stimulation element 610 may be implemented via at least some of substantially the same features and attributes as the cuff electrode 1220 described in association with at least FIGS. 17A-17C.

Meanwhile, the second distal portion 624 of main lead 620 may support at least one sensing element, such as sensing elements 631, 632.

It will be understood that throughout the various example implementations of the present disclosure, where one sensing element is provided, in some such examples multiple sensing elements may be provided. Moreover, in some such examples, where some multiple number (e.g. 2, 5, etc.) of sensing elements are shown on a lead, further examples may include more or fewer than the sensing elements shown in such Figures.

As further shown in FIG. 9, both the stimulation element 610 and the sensing element(s) 631, 632 may be implanted subcutaneously into the head-and-neck region 603 via the implant-access incision 100. Via this arrangement, the sensing elements 631, 632 are not implanted in a second (e.g. separate) implant-access incision separate from implant-access incision through which the stimulation element 610 is implanted, thereby simplifying the overall implantation method and/or device. In some examples, the sensing elements 631, 632 may sense CNS information, such as but not limited to EEG information. As noted elsewhere herein, in some examples the EEG information may comprise at least sleep state information and/or respiratory information for use in association with SDB care.

It will be understood that in some examples, the sensing elements 631, 632 may be implanted via a second (e.g. separate) implant-access incision in addition to implant-access incision 100, where the second implant-access incision is located at or near the intended final implantation location of the sensing elements 631, 632. One such example second/separate implant-access incision is later shown in at least the example arrangements of FIGS. 12-13A.

In some examples, the sensed CNS information may provide information suitable for sensing and evaluating sleep disordered breathing (SDB) information, which may relate to sleep quality, respiration, sleep disordered breathing events, and the like. In some examples, this sensed information may be used to modulate stimulation of a nerve 105 to treat sleep disordered breathing (SDB), which may comprise obstructive sleep apnea in some examples, with the nerve comprising an upper airway patency nerve, such as but not limited to the hypoglossal nerve. In some examples, the nerve 105 may comprise a phrenic nerve, which may be stimulated to treat central sleep apnea. In some examples, the sensed information may be used to modulate both stimulation of an upper airway patency nerve (e.g. hypoglossal nerve) and stimulation of a phrenic nerve (in a manner coordinated relative to each other) to treat sleep disordered breathing.

It will be understood that since respiratory information may be typically sensed in a torso body region, such as via a pressure sensor or trans-thoracic impedance sensor, being able to obtain respiratory information via sensing elements 631, 632 of an example device 602 located in the head-and-neck region 603 in close proximity to the stimulation element 610 would simplify implantation while still obtaining desired information. In particular, via such example arrangements, a much less invasive implantation method may be used in which a separate implant-access incision (previously used to implant respiratory sensing element(s)) may be omitted. Moreover, in addition to omitting the actual implant-access incision, such example arrangements also may avoid associated tunneling over longer distances in order to place respiratory sensing elements in locations within the torso region. In addition, in some instances, placing respiratory sensing elements in such torso locations may further comprise additional invasive implantation procedures in order to place the respiratory sensing element(s) in sensing-relation to the particular physiologic anatomy expected to produce the sensed respiratory information. However, via example arrangements of the present disclosure, such as but not limited to the example arrangement in FIG. 9, a less invasive procedure may be used via fewer implant-access incisions.

As further shown in FIG. 10, in some such example implementations of an example device 602, a compact implantation may be achieved. The arrangement 650 shown in FIG. 10 may comprise at least substantially the same features and attributes as the example arrangement shown and described in association with FIG. 9, except with a power/control element 655 being implanted via the single implant-access incision 100 and chronically implanted nearby the sensing elements 631, 632 (on lead portion 654) and the stimulation element 610. In some examples, the power/control element 655 may comprise a microstimulator, as more fully described in association with at least FIG. 4. In some such examples, the sensing elements, stimulation elements, power/control elements (e.g. microstimulator) are implanted to reside in their final implanted locations together within an area (represented via two dimensional circle A1) of less than on the order of 250 square centimeters (e.g. 245, 250, 255). In some examples, the volume A2 may be less than on the order of 275 square centimeters (e.g. 270, 275, 280), while in some examples, the volume A2 may be less than on the order of 300 square centimeters (e.g. 295, 300, 305). It will be understood that the area A1 may have a wide variety of shapes (e.g. oblong, elliptical, generally rectangular, triangular, etc.) in some examples, and is not necessarily a circular-shaped area as shown in FIG. 10, which is shown for illustrative simplicity.

In some examples, the area A1 (within which the respective elements have their final implant locations) may be less than on the order of 200 square centimeters (e.g. 195, 200, 205), while in some examples, the area A1 may be less than on the order of 150 square centimeters (e.g. 145, 150, 155).

In some examples, the area A1 may be less than on the order of 100 square centimeters (e.g. 95, 100, 105), while in some examples, the area A1 may be less than on the order of 75 square centimeters (e.g. 70, 75, 80).

In some examples, the area A1 may be less than on the order of 50 square centimeters (e.g. 45, 50, 55).

In some such examples, all of the sensing elements, stimulation elements, and power/control elements are located in their final implanted positions within a proximity of less than on the order of 6 inches (e.g. 5.8, 5.9, 6, 6.1, 6.2) relative to each other. In some examples the proximity may be less than on the order of 5 inches (e.g. 5.8, 5.9, 6, 6.1, 6.2) relative to each other. In some examples, the proximity may be less than on the order of 4 inches (e.g. 4.8, 4.9, 5, 5.1, 5.2) relative to each other, while in some examples, the proximity may be less than on the order of 3 inches (e.g. 3.8, 3.9, 4, 4.1, 4.2) relative to each other. In some examples, the proximity may be less than on the order of 2 inches (e.g. 1.8, 1.9, 2, 2.1, 2.2) relative to each other.

In some such examples, instead of comprising sensing elements 631, 632 separate from a stimulation element 610, a compact implantation may be implemented and enhanced via use of a single electrode element to sense EEG and to stimulate upper airway patency nerve (e.g. hypoglossal nerve). For instance, the sensing elements 631, 632 may be omitted and the stimulation element 610 may also act as a sensing element in addition to its role in delivering stimulation. In such instances, the element 610 may sense physiologic information other than, or in addition, to sensing EEG information. In some such examples of compact implantation in the head-and-neck region, the implantable device comprises a torso-free device in which no components are located in the patient's torso region.

In some such examples, the single element used for both sensing and stimulation may comprise a stimulation electrode in stimulating-relation to a nerve (e.g. upper airway patency nerve) in a position external to a patient's brain, and from which sensing of EEG information may be performed. In some such examples, the stimulation electrode element may be located in a mandible-neck area 607 and the same electrode(s) may be used to sense EEG information. In some such examples, the combined sensing and stimulation element may obtain EEG information via single channel EEG sensing.

In some of the examples preceding examples and/or later examples in which a single element (e.g. stimulation element 610) is used for both sensing (e.g. EEG) and stimulation (e.g. of hypoglossal nerve), the stimulation element 610 may be implemented to perform both sensing and stimulation via at least some of substantially the same features and attributes as the electrode arrangements described in association with at least FIGS. 17A-17C.

Figure 11:
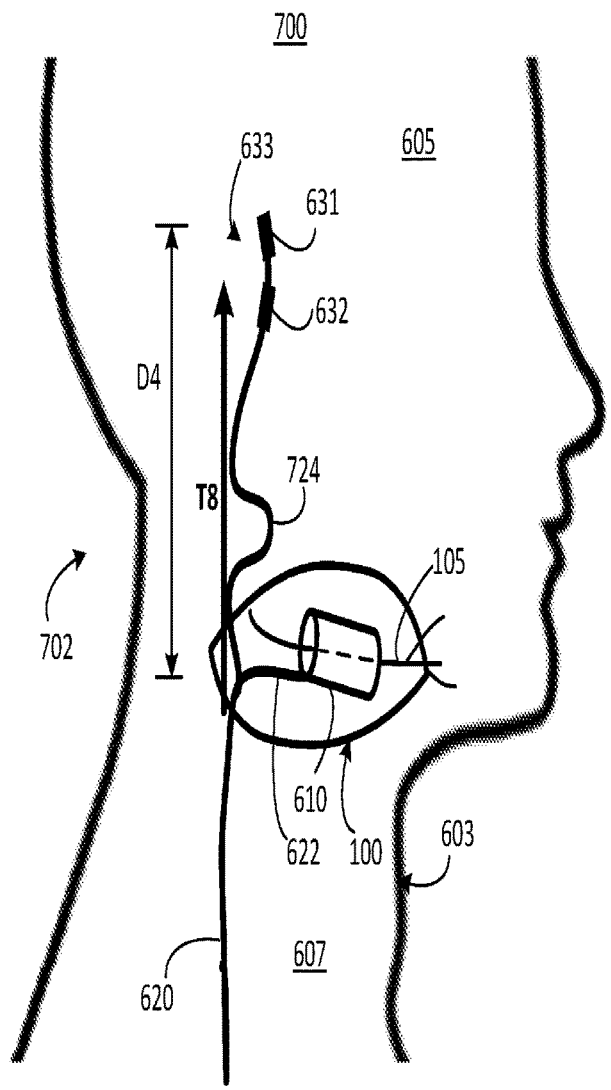
FIG. 11 is a diagram including a top view schematically representing an example device and/or example method including implanting, via a first implant-access incision in a first body region, both a stimulation element and sensing elements.

FIG. 11 is a diagram 700 schematically representing an example method 702 and/or device comprising implantation of at least a first element and a second element within a patient's body. In some examples, device and/or method 702 may comprise at least some of substantially the same features and attributes as method 602 in FIGS. 9-10, except for sensing elements 631, 632 being implanted a further distance away from the implant-access incision 100. In particular, in the example of FIG. 11, second distal portion 624 is replaced via a longer second distal lead portion 724 which enables placing sensing elements 631, 632 at a distance D4 spaced apart from the first element 610 and the implant-access incision 100. In some such examples, this arrangement enables placing the sensing elements 631, 632 in close proximity to sensing particular physiologic information without forming an incision at the final implant location 633 of the sensing elements 631, 632. Among other aspects, this arrangement may enhance the appearance of the patient, expedite healing, etc. In some such examples, the particular physiologic information obtained via sensing elements 631, 632 may comprise particular EEG signals generally known to traverse a particular portion of the cranium. In such examples, the distal lead portion 724 and associated sensing elements 631, 632 are tunneled subcutaneously as schematically represented via indicator T8. In some such examples, prior to maneuvering the sensing elements 631, 632 (on distal lead portion 724) to their target location, various tunneling tools may be used to create a tunnel (T8) to ease passage of the sensing elements 631, 632 and second distal portion 724 of lead 620.

In some examples, the distance D4 of separation between sensing elements 631, 632 and the implant-access incision 100 (with element 610) according to the incision-less implantation of sensing element 631, 632 (for placement at its final implant location) comprises at least some of substantially the same features and attributes as the distance of separation (e.g. D1, D2, D3) as previously described in association with at least FIGS. 2, 6, and 8, respectively.

Figure 12:
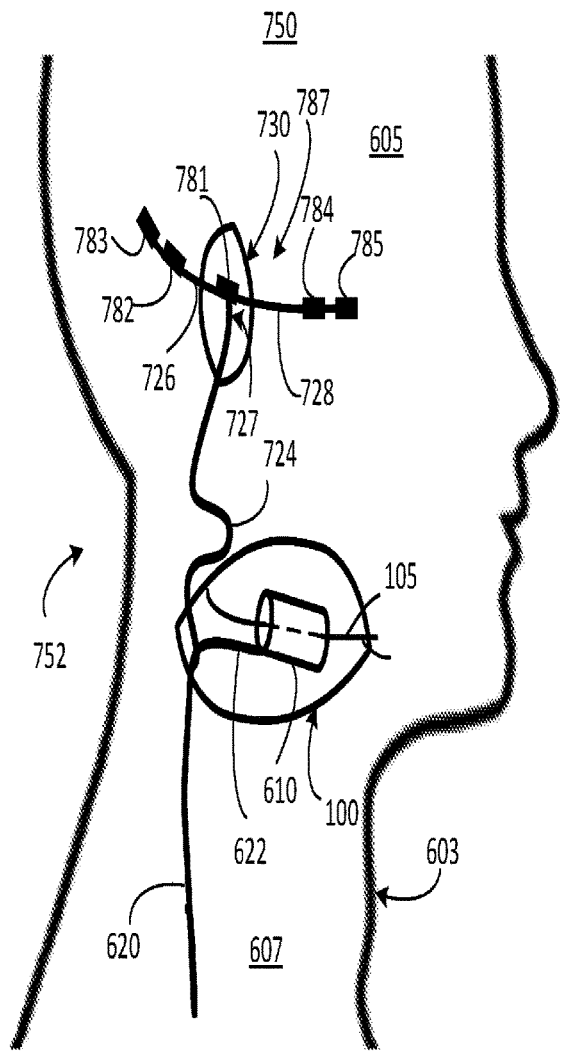
FIG. 12 is a diagram including a top view schematically representing an example device and/or example method including implanting, via a first implant-access incision in a neck-mandible region, a stimulation element and implanting, via a second implant access-incision in a cranial region, sensing elements.

FIG. 12 is a diagram 750 schematically representing an example method 752 and/or device comprising implantation of at least a first element and a second element within a patient's body. In some examples, device and/or method 752 may comprise at least some of substantially the same features and attributes as method 702 in FIG. 11, except for comprising at least some of additional sensing elements 781-785 of a sensing arrangement 787 on distal lead portion 724 replacing sensing elements 631, 632 (FIG. 11) and being implanted via a separate implant-access-incision 730 in addition to implant-access incision 100. In some examples, the first distal lead portion 724 comprises a bifurcated arrangement including distal extensions 726, 728, which may extend in opposite directions. In some such examples, the first distal extension 726 may support sensing elements 782, 783 while the second distal extension 728 may support sensing elements 784, 785. In some examples, sensing element 781 may be supported along first distal extension 724, along second distal extension 726, or as shown in in FIG. 12, the sensing element 781 may be supported by a junction 727 of the respective distal extensions 724, 726.

Figure 13A:
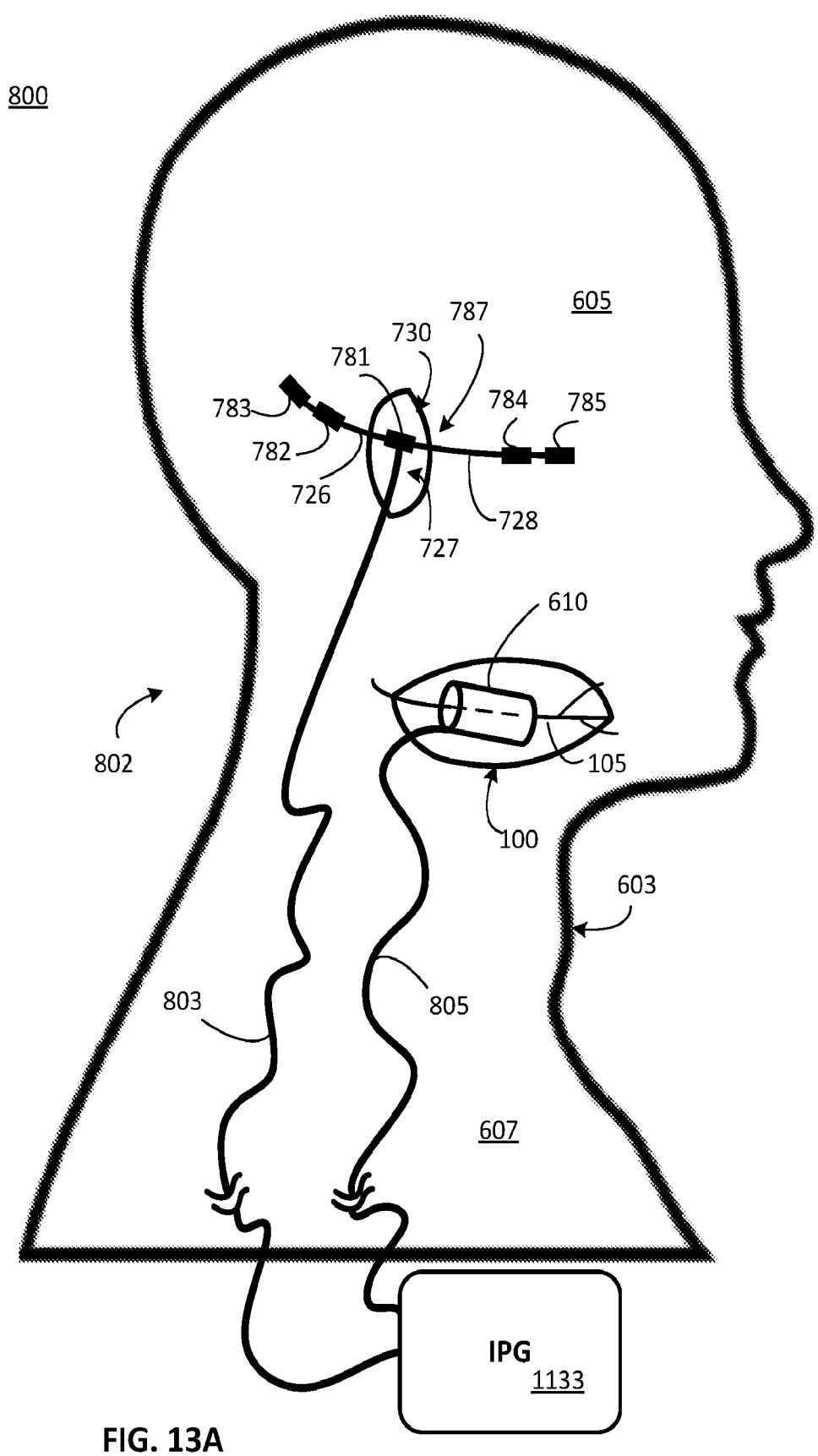
FIG. 13A is a diagram including a top view schematically representing an example device and/or example method including: implanting, via a first implant-access incision in a neck-mandible region, a stimulation element; implanting, via a second implant access-incision in a cranial region, sensing elements; and implanting a power/control element in another body region.

FIG. 13A is a diagram 800 schematically representing an example method 802 and/or device comprising implantation of at least a first element and a second element within a patient's body. In some examples, device and/or method 802 may comprise at least some of substantially the same features and attributes as method 702, 752 in FIGS. 11-12, except for the additional sensing elements 781-785 (of sensing arrangement 787) on distal lead portion 803 being implanted via a separate implant-access-incision 730 and distal lead portion 805 being electrically connected to a torso-located pulse generator (or monitoring device) 1133. In some such examples, distal lead portion 803 is tunneled subcutaneously from implant-access incision 730 to the torso-located pulse generator (or monitoring device) 1133 separate form, and independent of, lead portion 805 which is tunneled subcutaneously between implant-access incision 100 and the pulse generator (or monitoring device) 1133. While not shown for illustrative simplicity, it will be understood that a separate implant-access incision (e.g. 313 in FIGS. 5-8) may be formed to implant the pulse generator 1133 and facilitate tunneling (like T3, T4 in FIGS. 5, 8 as one example) relative to the other respective implant-access incisions 730, 100. In some such examples, blunt dissection may be used to add one or more branches of sensing elements under the skin, which may be used in association with a short insertion distance.

Figure 13B:
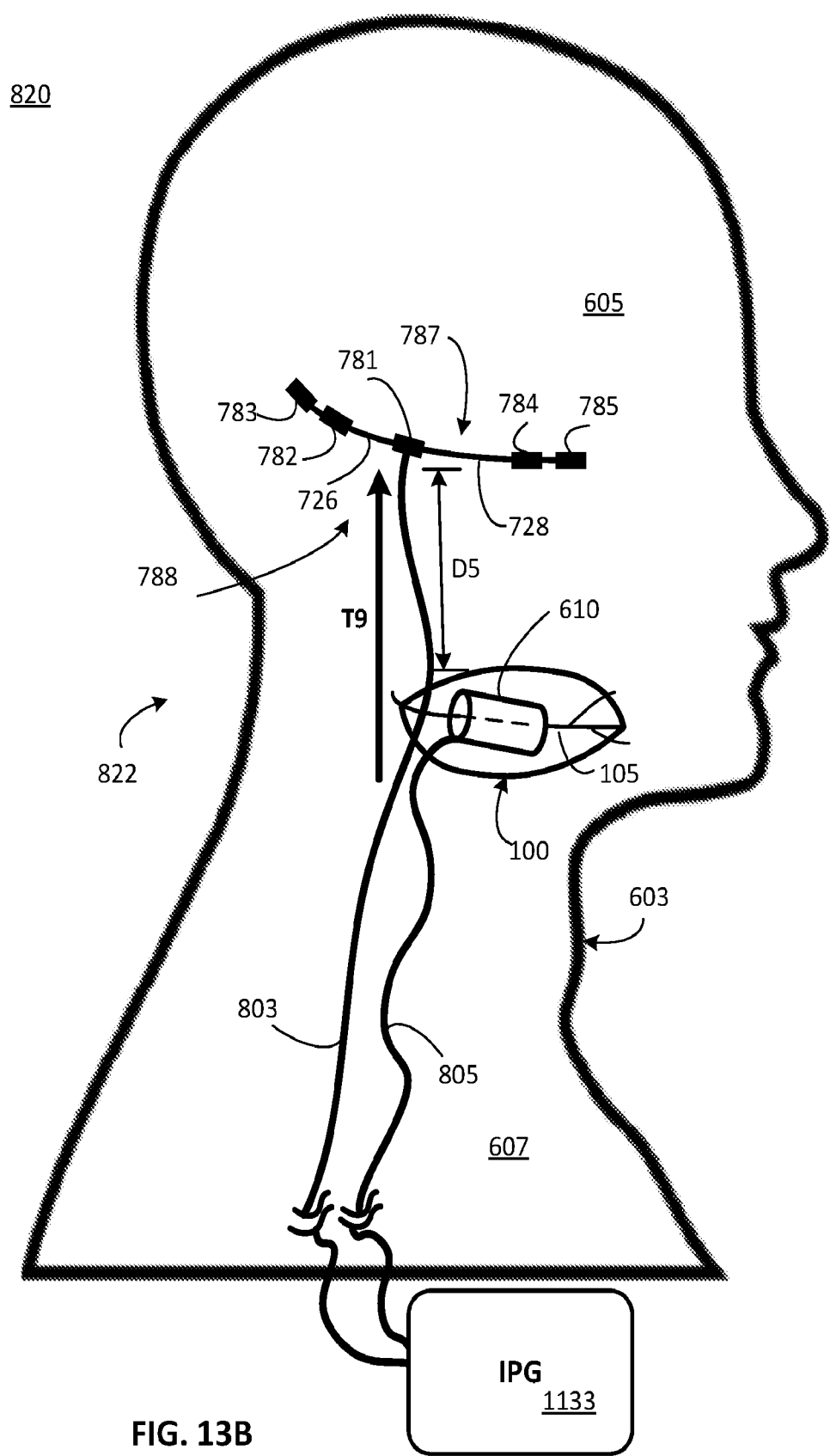
FIG. 13B is a diagram including a top view schematically representing an example device and/or example method including: implanting, via a first implant-access incision in a neck-mandible region, a stimulation element in neck-mandible region and sensing elements in a cranial region, sensing elements; and implanting a power/control element in another body region.

FIG. 13B is a diagram 820 schematically representing an example method 822 and/or device comprising at least some of substantially the same features and attributes as method 802 in FIG. 13A, except for at least omitting separate implant-access incision 730. In some such example implementations, the distal lead portion 803 and sensor arrangement 787 may be placed in their final implant location shown in FIG. 13B via tunneling from an implant-access incision for implanting IPG 1133 or via tunneling (arrow T9) from implant-access incision 100. In the latter example, the lead 803 may be physically paired with lead 805 such that a single tunnel/path may be formed between the IPG 1133 and the implant-access incision 100, with the lead 803 being extended further by distance D5 subcutaneously in the head portion 605 from the implant-access incision 100.

In some such examples, the sensor lead portion 803 may be configured to extend distally from the sensor lead portion 805 such that the sensor lead portion 803 is separate from the sensor lead portion 805 solely in the head portion 605 distally of the implant-access incision 100.

In some examples associated with FIG. 13B, the distance D5 between the final implant location 788 and implant-access incision 100 may comprise at least some of substantially the same features and attributes as the distance (e.g. D1, D2, D3, etc.) relationships (e.g. remote spacing) as previously described in association with at least FIGS. 2, 6, 8, etc.

Figure 13C:
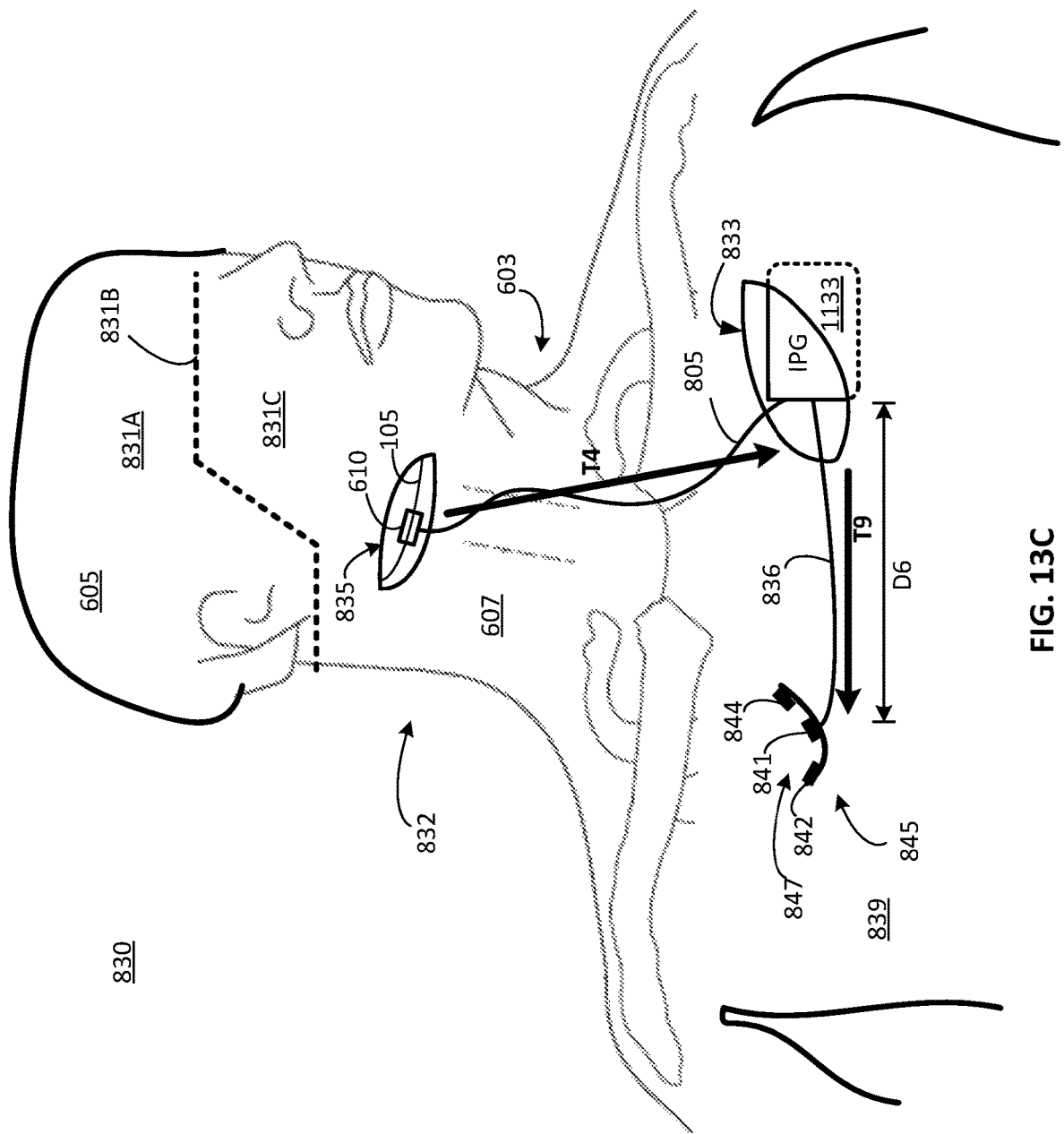
FIG. 13C is a diagram including a top view schematically representing an example device and/or example method including: implanting, via a first implant-access incision in a neck-mandible region, a stimulation element; implanting, via a second implant access-incision in a pectoral region, sensing elements and implanting a power/control element.

FIG. 13C is a diagram 830 schematically representing an example method 832 and/or device to treat sleep disordered breathing (SDB), such as but not limited to obstructive sleep apnea. In some examples, the method and/or device may comprise at least some of substantially the same features and attributes as method 822 in FIG. 13B, except comprising a sensor arrangement 847 (on lead 836) placed in a final implant location 845 in the torso region 839 instead of having a final implant location in the cranium portion 831A (FIG. 13C) of the head-and-neck region 603 as in FIG. 13C. As further shown in FIG. 13C, the cranium portion 831A of the head-and-neck region 603 is separate and distinct from (as schematically represented via separation line 831B) the non-cranium portion 831C of the head-and-neck region 603, which includes the face, mandible, neck, etc.

In some examples, the sensor arrangement 847 may comprise an array of sensing elements 841, 842, 844 like sensing elements 781-785 of sensing arrangement 787 in FIG. 13B. However, in some such examples, the sensor arrangement 847 may comprise fewer or more sensing elements than in FIG. 13B and/or may comprise a different spatial configuration of such sensing elements.

As shown in FIG. 13C, method 832 may comprise an implant-access incision 835 similar to implant-access incision 100 (e.g. FIG. 13A, 13B) and by which at least stimulation element 610 (supported on lead 805) may be placed in its final implant location 835 shown in FIG. 13C and by which lead 805 may be tunneled (T4) relative to the final implant location (at/near implant-access incision 833) of the IPG 1133. In some examples in which the implant-access incision 835 may sometimes be referred to as a first implant-access incision, then the implant-access incision 833 may be referred to as a second implant-access incision.

In some examples, the sensor arrangement 847 may sense at least respiratory information, which may be used to sense, determine, and/or evaluate sleep disordered breathing (SDB) behavior, sleep quality information, respiratory cycle information, etc. In some such examples, this sensed respiratory information may be used to initiate, terminate, and/or adjust stimulation of an upper airway patency nerve as part of treating obstructive sleep apnea. In some such examples, this sensed respiratory information may be used to trigger and/or implementing timing of the neurostimulation signal applied to the upper airway patency nerve.

In some examples, the sensing arrangement 847 may be used to sense impedance, such as transthoracic impedance, which in turn may be used to obtain respiratory information, sleep quality information, sleep disordered breathing (SDB) information, etc. In some examples, the sensing arrangement 847 may be used to obtain EEG information, which may in some examples, include respiratory information.

In some examples, the IPG 1133 (e.g. power/control element) in the example arrangement of FIG. 13C may be placed in its final implant location via an implant-access incision 833 similar to a torso-located implant-access incision (e.g. 313 in FIGS. 7-8).

In some examples, in addition to or as an alternative to the sensing arrangement 847 and lead 836 shown in FIG. 13C, other and/or additional elements of the example arrangement in FIG. 13C may be used to sense impedance to obtain respiratory information. For instance, the stimulation element 610 also may be used as an electrically conductive sensing element and at least an electrically conductive portion(s) of an exterior (e.g. case) of the IPG 1133 may be used together to sense thoracic impedance. In some such examples, when the impedance vector between element 610 and the IPG 1133 is utilized in combination with the sensing arrangement 847, a wide variety of impedance vectors may be implemented among element 610, IPG 1133, and/or the sensing elements (e.g. 841, 842, and/or 844) of the sensing arrangement 847.

In some examples, the sensing arrangement 847 may be implemented as a respiratory pressure sensor implanted via implant-access incision 833 for IPG 1133, with lead 836 supporting the respiratory pressure sensor. In some such examples, the respiratory pressure sensor may comprise at least some of substantially the same features and attributes as described in Christopherson et al., US Patent Publication US2011/0152706, METHOD AND APPARATUS FOR SENSING RESPIRATORY PRESSURE IN AN IMPLANTABLE STIMULATION SYSTEM, published on Jun. 23, 2011, and/or in Verzal et al., U.S. Patent Publication 2019/0344084, MEDICAL DEVICE INCLUDING TOOL-GRIPPING PORTION, published on Nov. 14, 2019, each of which are incorporated herein by reference in their entirety.

In some examples, the sensing arrangement 847 may be implemented as an accelerometer implanted via implant-access incision 833 to sense at least respiratory information as previously described above. In some such examples, this sensed respiratory information may be used to sense, determine, and/or evaluate sleep disordered breathing (SDB) behavior. In some such examples, this sensed respiratory information may be used to initiate, terminate, and/or adjust stimulation of an upper airway patency nerve as part of treating obstructive sleep apnea. In some such examples, this sensed respiratory information may be used to trigger and/or implementing timing of the neurostimulation signal applied to the upper airway patency nerve. For instance, this sensed respiratory information may be used to synchronize the stimulation signal with a portion of a sensed respiratory cycle, such as the sensed inspiratory phase and/or other sensed respiratory cycle information. In some examples, the accelerometer and associated respiratory sensing may be implemented according to at least some of substantially the same features and attributes as described in U.S. Patent Publication US2019/0160282, ACCELEROMETER-BASED SENSING FOR SLEEP DISORDERED BREATHING (SDB) CARE, published on May 30, 2019, and previously published as PCT Publication WO2017/184753, ACCELEROMETER-BASED SENSING FOR SLEEP DISORDERED BREATHING (SDB) CARE, on Oct. 26, 2017, both of which are incorporated by reference herein in their entirety.

In some examples, the placement of the sensor arrangement 847 (or other sensing element) may sometimes be referred to as incision-less chronic subdermal implantation in that a separate implant-access incision is not formed to place the sensor arrangement at its final implant location 845 remote from the IPG 1133. Instead, via tunneling and/or similar techniques to provide a subcutaneous pathway, the sensor arrangement 847 is inserted into and through the implant-access incision 100 and then advanced subcutaneously (represented by directional arrow T9) toward and up to its final implant location 845. This example arrangement avoids making a separate incision in the patient's skin at or near the final implant location 845 of the sensing element (e.g. sensor arrangement 847), thereby reducing the overall invasiveness of the implantation method. For instance, by avoiding making an incision at or near the final implant location of the sensing element, one can reduce the exposure of the subcutaneous tissue to the ambient environment during surgical implantation, maintain the cosmetic appearance of the patient, etc.

In some examples associated with FIG. 13C, the distance (D6) between the final implant location 845 of the sensor arrangement 847 and the implant-access incision 833 (and the IPG 1133) may comprise at least some of substantially the same attributes as the distance (e.g. D1, D2, D3, etc.) relationships (e.g. remote spacing) as previously described in association with at least FIGS. 2, 6, 8, etc.

It will be understood that in some examples, the sensing arrangement 847 (or substitute sensing element such as respiratory pressure sensor) may be placed in a wide variety of locations about the torso such that tunneling (T9) may be implemented in any radial orientation relative to implant-access incision 833, and is not limited to the particular example orientation shown in FIG. 13C in which the tunneling (and lead 836) extends across the chest.

Figure 14A:
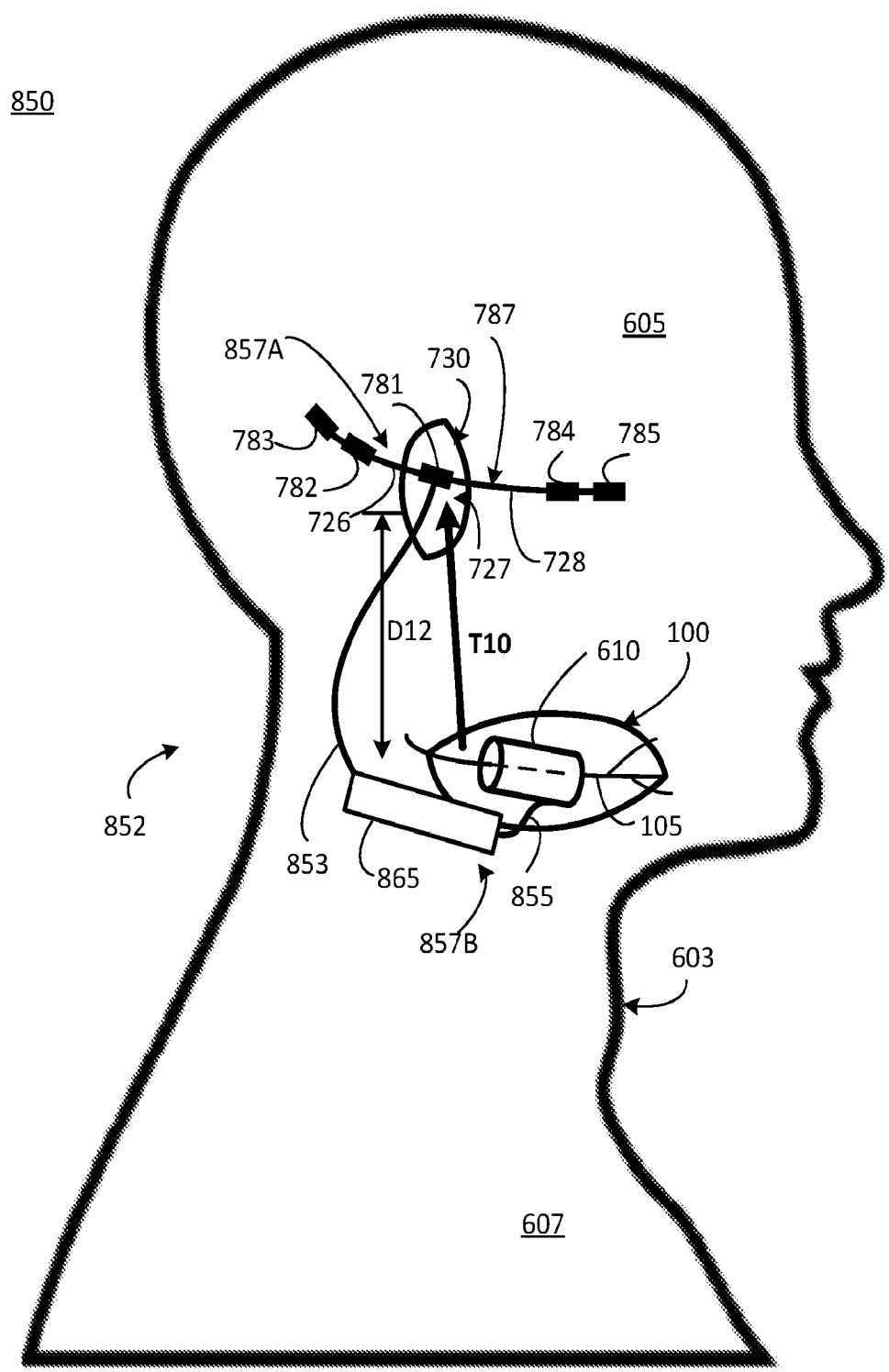
FIG. 14A is a diagram including a side view schematically representing an example device and/or example method including: implanting, via a first implant-access incision in a neck-mandible region, a stimulation element and a power/control element; and implanting, via a second implant access-incision in a cranial region, sensing elements.

FIG. 14A is a diagram 850 schematically representing an example method 852 and/or device comprising implantation of at least a first element and a second element within a patient's body. In some examples, device and/or method 802 may comprise at least some of substantially the same features and attributes as method 802 in FIG. 13A or 13B, except comprising a power/control element 865 located in close proximity to stimulation element 610 and placed into its final location in the mandible-neck portion 607 of the neck-head region 603 via implant-access incision 100. This arrangement stands in contrast to the example arrangement in FIGS. 13A-13B in which a pulse generator 1133 is located in the torso region and may be implanted via an implant-access incision 833, which is separate from implant-access incision 100.

It will be understood that in some such examples the power/control element 865 may comprise a microstimulator, as described in association with at least FIG. 4. Moreover, in some such examples, the power/control element 865 and the stimulation element 610 may be combined into a single element, such as with stimulation element comprising an electrode exposed or mounted on an outer surface of a housing of the power/control element 865. In such examples, lead portion 855 is omitted, thereby simplifying insertion and arranging the combined stimulation element and power/control element into their final implanted location.

In some such examples, a sensor arrangement 787 including various sensing elements 781-785 may be supported by lead portion 853, which extends from and is electrically connected to the power/control element 865. In some such examples, the sensor arrangement 787 may be placed into its final implant location 857A via implant-access incision 730 with lead 853 being tunneled subcutaneously (as represented by T10) between the respective implant-access incisions 100 and 730.

Moreover, in some examples, method 852 may comprise omitting the implant-access incision 730 in order to implant a sensing element(s) in the head portion 605 (e.g. cranium portion 831A in FIG. 13C) via use of an incision-less implantation of the sensing element, in a manner involving at least some of substantially the same features and attributes as the method 832 in FIG. 13C at least regarding implantation of sensing arrangement 847. It will be understood that in some examples the sensing arrangement 787 in FIG. 14A may be implemented via a smaller configuration and/or with fewer sensing elements than shown in FIG. 14A in order to implement the incision-less implantation as appropriate. In some such examples, an incision-free final implant location 857A of the chronically subdermally implanted sensing arrangement 787 (or simpler sensing element) may be spaced apart from the implant-access incision 100 (and the final "mandible-neck" implant location 857B of microstimulator 865) by a distance D12. In some examples, the distance D12 may comprise at least some of the substantially same features and attributes as the distance (e.g. D1, D2, D3, etc.) relationships (e.g. remote spacing) as previously described in association with at least FIGS. 2, 6, 8, 13C, etc.

Figures 14B, 14C:
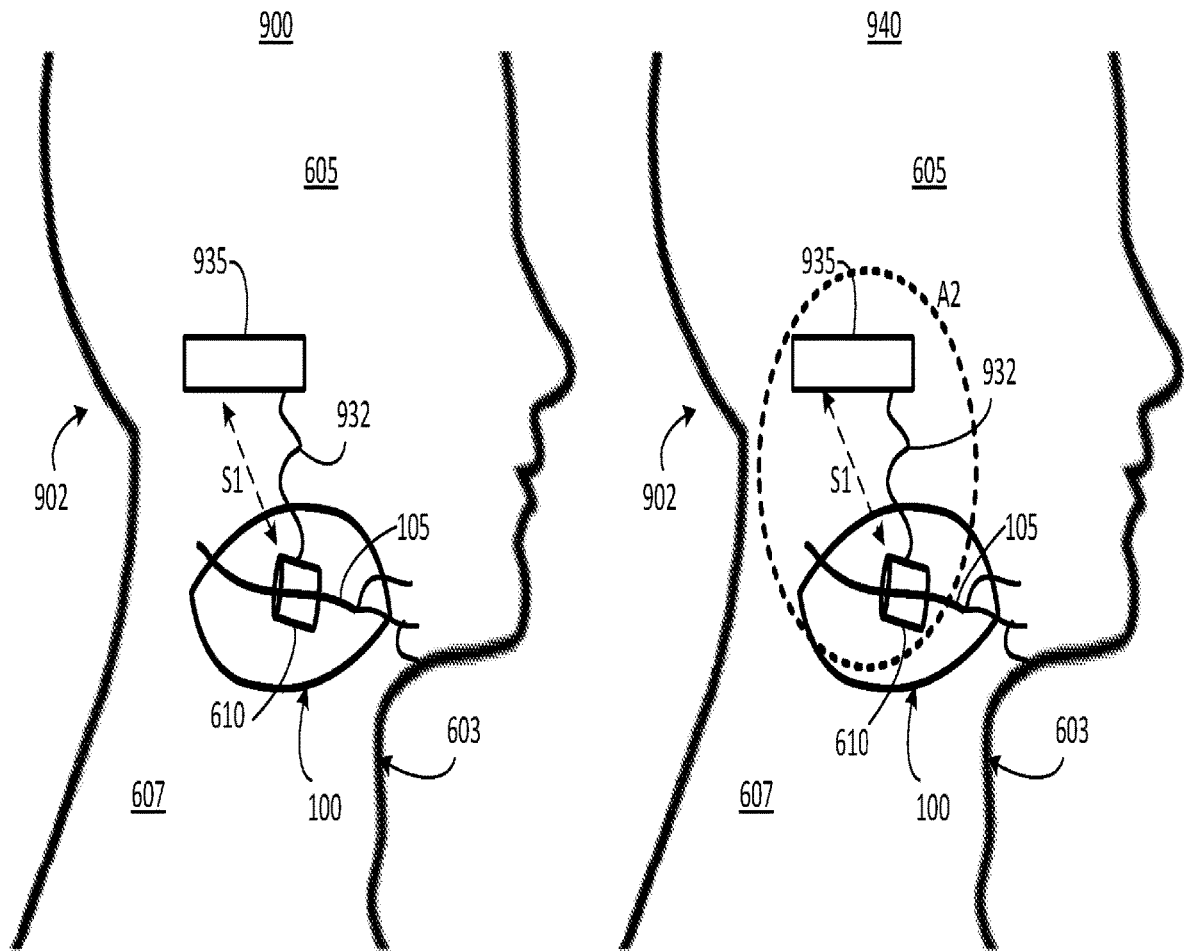
FIGS. 14B and 14C are each a diagram including a side view schematically representing an example device and/or example method including: implanting, via a first implant-access incision in a neck-mandible region, a stimulation element and a power/control element.

FIG. 14B is a diagram 900 schematically representing an example method 902 and/or device comprising implantation of at least a first element and a second element within a patient's body. As shown in FIG. 14B, in some examples method 902 may comprise a single implant-access incision 100 to place a stimulation element 610 in stimulating-relation relative to a nerve 105, which may comprise an upper airway patency nerve in some examples. Via the single implant-access incision 100, a microstimulator 935 may be implanted in proximity to the stimulation element 610, which may be electrically connected to the microstimulator 935 either via a lead 932 or wirelessly. In some such examples, an electrically conductive portion (e.g. housing, externally exposed electrode, etc.) of the microstimulator 935 and the stimulation element 610 may form a sensing vector S1 by which physiologic signals (e.g. EEG signals) in the head-and-neck region 603 may be sensed. At least some example implementations for such sensing are described in association with at least FIGS. 17A-17C. In some examples, the microstimulator 935 may use such sensed physiologic information (e.g. EEG signals) to modulate stimulation signals delivered from microstimulator 935, via lead 932 or wirelessly, to nerve 105 via stimulation element 610. In some examples, a separate patient-external monitor and/or the microstimulator 935 may use the sensed physiologic information to monitor physiologic conditions (with or without stimulation), diagnose conditions, evaluate stimulation therapy, initiate or terminate stimulation therapy, and the like.

However, in some examples, the position of the microstimulator 935 and the element 610 may be switched and with the element 610 formed and acting as a sensing element and with the microstimulator 935 placed into stimulating-relation relative to the nerve 105. As before, a sensing vector S1 may be formed between the element 610 (as a sensing element) and the microstimulator 935.

Via such example arrangements, a device and/or method to treat sleep disordered breathing (or other conditions) may be implemented in a minimally invasive manner which uses fewer implant-access incisions and/or less tunneling of leads between different components (e.g. sensing elements, stimulation elements, pulse generator, monitor) of a device. Moreover, via such an example arrangement, all of the major components (e.g. sensing, stimulation, power/control) of the device (or used in a method) are located within a single patient body region, such as the head-and-neck region.

As further shown in the diagram 940 of FIG. 14C, in some such example implementations of an example device 902, a compact implantation may be achieved. For instance, in some examples, the elements to implement stimulation generation (e.g. power/control), the elements to implement sensing and the elements to implement stimulation (e.g. a stimulation electrode) are implanted within an area (represented via two dimensional circle A2) of less than on the order of 250 square centimeters (e.g. 245, 250, 255). It will be understood that the area A2 may have a wide variety of shapes in some examples, and is not necessarily a circular-shaped area as shown in FIG. 14C, which is shown for illustrative simplicity.

In some examples, the area A2 may be less than on the order of 200 square centimeters (e.g. 195, 200, 205), while in some examples, the area A2 may be less than on the order of 150 square centimeters (e.g. 145, 150, 155).

In some examples, the area A2 may be less than on the order of 100 square centimeters (e.g. 95, 100, 105), while in some examples, the area A2 may be less than on the order of 75 square centimeters (e.g. 70, 75, 80).

In some examples, the area A2 may be less than on the order of 50 square centimeters (e.g. 45, 50, 55).

In some such examples, all of the sensing elements, stimulation elements, and power/control elements in FIG. 14B are located in their final implanted positions within a proximity of less than on the order of 6 inches (e.g. 5.8, 5.9, 6, 6.1, 6.2) relative to each other. In some examples the proximity may be less than on the order of 5 inches (e.g. 5.8, 5.9, 6, 6.1, 6.2) relative to each other. In some examples, the proximity may be less than on the order of 4 inches (e.g. 4.8, 4.9, 5, 5.1, 5.2) relative to each other, while in some examples, the proximity may be less than on the order of 3 inches (e.g. 3.8, 3.9, 4, 4.1, 4.2) relative to each other. In some examples, the proximity may be less than on the order of 2 inches (e.g. 1.8, 1.9, 2, 2.1, 2.2) relative to each other.

Even with this relative consolidation of the major components of a device (and/or method) in a first patient body region, physiologic information primarily associated with other (e.g. second) patient body regions may still be obtained via the first patient body region and used as part of diagnosis, monitoring, and/or therapy. For example, with all the major components located in the head-and-neck region (e.g. 603), physiologic information primarily associated with a torso region, such as (but not limited to) respiratory information, may still be obtained via elements in the head-and-neck region and/or used as part of diagnosis, monitoring, and/or therapy.

Figure 15:
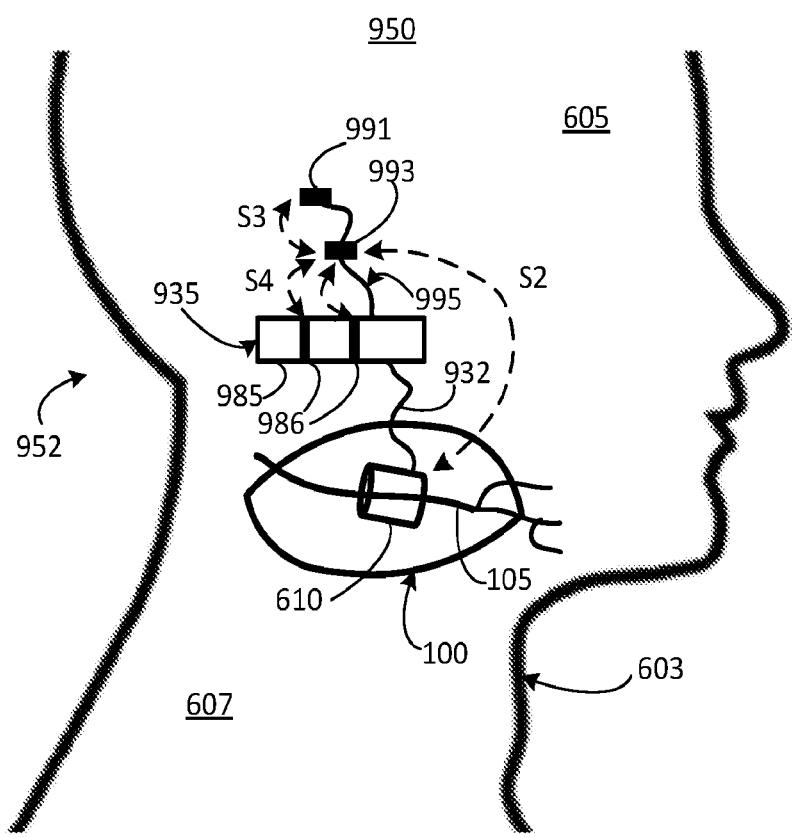
FIG. 15 is a diagram including a side view schematically representing an example device and/or example method including: implanting, via a first implant-access incision in a neck-mandible region, a stimulation element in the neck-mandible region, a power/control element, and sensing elements.

FIG. 15 is a diagram 950 schematically representing an example method 952 and/or device comprising implantation of at least a first element and a second element within a patient's body. In some examples, device and/or method 952 may comprise at least some of substantially the same features and attributes as method 902 in FIG. 14B, except for further comprising the extension of additional sensing elements 991, 993 extending (via lead 995) from the microstimulator 935 further for subdermal implantation (i.e. not intracranial) into a cranial portion 605 of the head-and-neck region 603. In addition, in some such examples the microstimulator 935 may comprise additional sensing elements 986 on a surface 985 of a housing of the microstimulator 935. In some such examples, via this arrangement sensing vector(s) (e.g. S2) may be formed between the stimulation element 610 (at nerve 105) and the sensing element(s) 991, 993 and/or sensing vector(s) (e.g. S3, S4) may be formed between the sensing elements 991, 993 and the sensing element(s) 986 on the surface 985 of microstimulator 935. Moreover, in some such examples, sensing vector(s) also may be formed between the sensing element(s) 986 on the microstimulator 935 and stimulation element 610. At least some example implementations of such arrangements are described later in association with at least FIGS. 17A-17C.

Via at least some such example sensing vectors and example sensing element arrangements, the method and/or device 952 (FIG. 15) may be implemented in a manner to account for variability in patient anatomy, variability in patient physiological conditions, variability in patient therapeutic strategies, and/or variability in surgical procedures, surgeons, etc. In some example implementations of method 952 (and/or device), a compact implantation may be achieved comprising at least some of substantially the same features and attributes as previously described in association with FIG. 14C, FIG. 10, etc., such as a final implantation of the respective sensing, stimulation, power/control elements fitting within an area A1 or A2 similar to that shown in previous Figures.

Figure 16A:
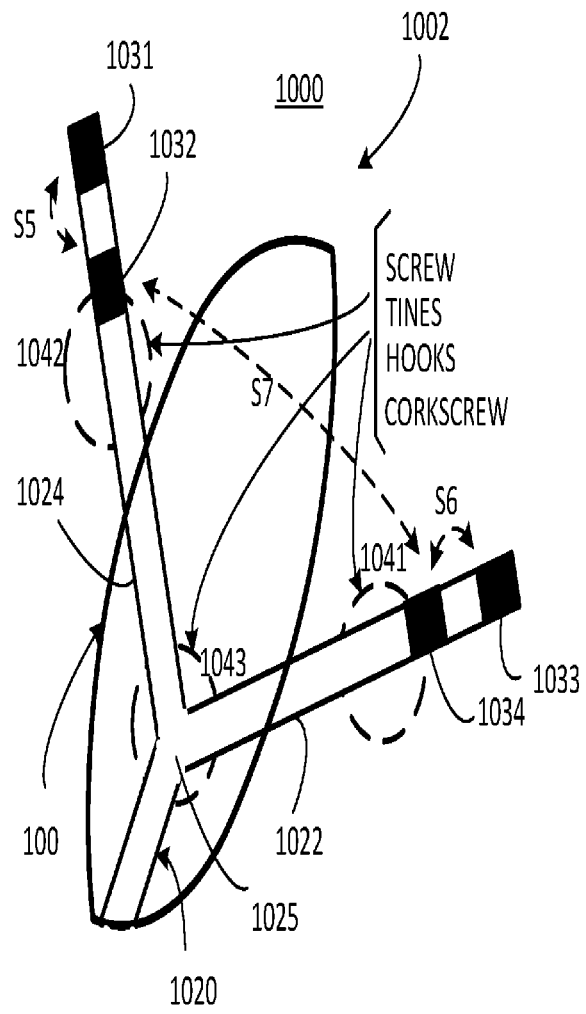
FIGS. 16A and 16B are each a diagram including side view schematically representing an example device and/or example method including implantation, via an implant-access incision, of sensing elements using fixation elements.

FIG. 16A is a diagram 1000 schematically representing an example method 1002 and/or device involving implantation of at least some sensing and/or stimulation elements, such as elements 1031, 1032, 1033, and/or 1034. In some examples, the method (and/or device) 1002 comprises an example implementation of at least some of substantially the same features and attributes as one or several example methods/devices as previously described in association with at least FIGS. 1-15. For instance, as shown in FIG. 16A, in some examples, sensing elements 1031, 1032, 1033, and/or 1034 may be implanted via an implant-access incision 100 located in a patient body region. Some of the sensing elements (e.g. 1031, 1032) may be located on one distal extension 1024 of lead 1020 while some sensing elements (e.g. 1033, 1034) may be located on a separate distal extension 1022 of lead 1020. Whether lead 1020 comprises separate (e.g. bifurcated) distal extensions or a single distal extension, in some examples the method (and/or device) 1002 may comprise fixation element(s) 1041, 1042, and/or 1043 to facilitate securing the respective distal extension(s) 1022, 1024 relative to tissue within a patient body region. In some examples, such tissue may comprise a bony structure and/or non-bony structures, such as tendons and the like.

As shown in FIG. 16A, in some examples the fixation element(s) 1041, 1042, and/or 1043 may comprise a fixation structure suitable for the type of tissue available for securing the distal extension, such as a screw (e.g. bony structures), tines, hooks, corkscrew. In some examples, at least some of the fixation elements (e.g. tines, hooks) may sometimes be referred to as passive fixation elements at least because they may be self-deploying as the distal extension (e.g. 1022, 1024) is implanted in a target location via an implant-access incision 100. Meanwhile, some fixation elements, such as a screw involve more active attention to implement fixation of the distal extensions 1022, 1024.

Figure 16B:
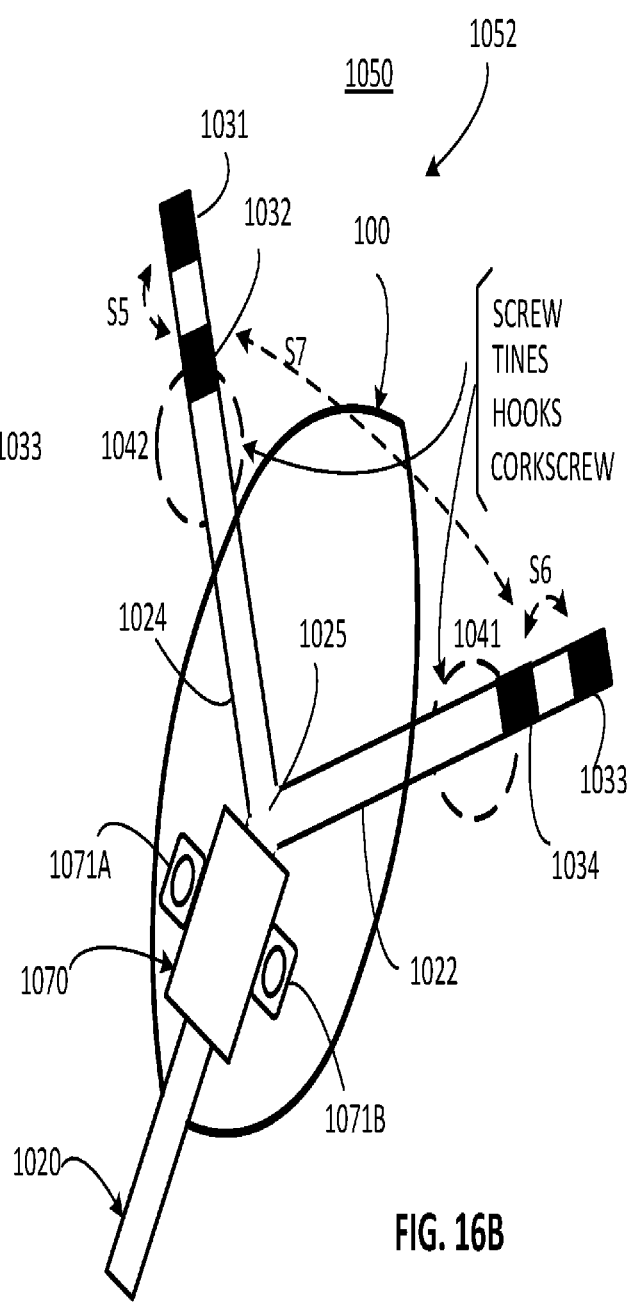

FIG. 16B is a diagram 1050 schematically representing an example method 1052 (and/or device). In some examples, method 1052 (and/or device) may comprise at least some of substantially the same features and attributes as method 1002, except with one or more of the fixation element(s) being replaced by an anchor 1070, which may be suturable or otherwise secured (e.g. screw) via holes 1071A, 1071B. In some examples, the anchor 1070 is implemented on main lead 1020 adjacent a junction 1025 from which separate distal extensions 1022, 1024 extend. Via such arrangements, in some examples both distal extensions 1022, 1024 may be more stably fixed.

As further shown in FIGS. 16A-16B, in some examples one or more sensing vectors (e.g. S5, S6, and/or S7) may be formed among the sensing element(s) 1031, 1032, 1033, and/or 1034. In addition or alternatively, one or more sensing vector(s) may be formed from the sensing element(s) 1031, 1032, 1033, and/or 1034 and another element located elsewhere, such as a stimulation element (e.g. 610 in FIGS. 10B-15), case or housing of a pulse generator (e.g. 1133 in FIG. 13) or microstimulator (e.g. 935 in FIGS. 14A, 14B).

It also will be understood that at least some of the various fixation elements described and illustrated in association with at least FIGS. 16A-16B may be utilized in any one of the various examples of the present disclosure to secure a sensing element, a stimulation element, associated lead, etc.

to maintain the respective sensing element, stimulation element, associated lead, etc. in a targeted final implant location.

Figure 17A:
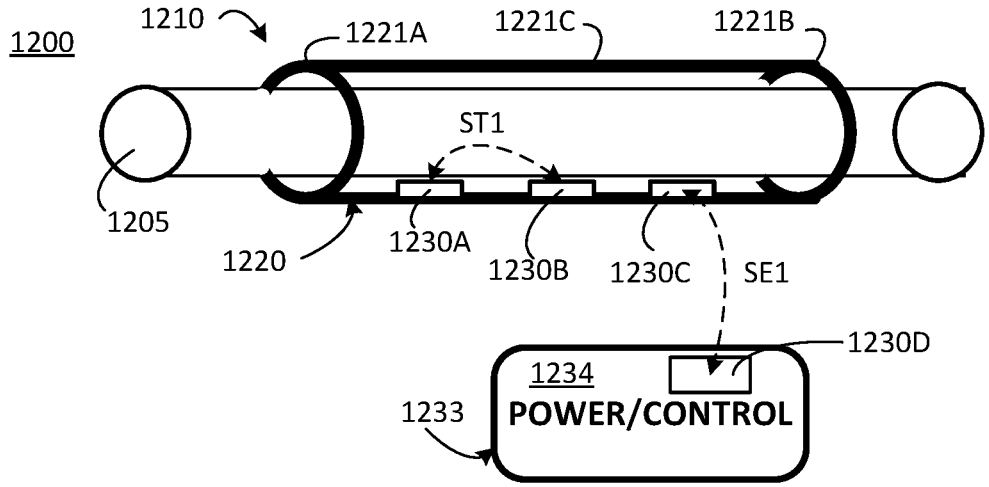
FIGS. 17A and 17B are each a diagram including side view schematically representing an example device and/or example method including a cuff electrode with multiple electrodes and a power control element.

FIG. 17A is diagram 1200 schematically representing one example arrangement 1210 including an array of electrodes which may act as a first element (e.g. 110) and/or a second element (e.g. 120), such as when the first element comprises a sensing element and the second element comprises a stimulation element, and variations thereof. In some examples, the arrangement 1210 may comprise at least some of substantially the same features and attributes as, or comprise an example implementation of, one or more of the example first elements and/or second elements as previously described in association with FIGS. 1-16B.

In one aspect, the example arrangement 1210 comprises a cuff electrode 1220 including a cuff body 1221C extending between opposite ends 1221A, 1221B with cuff body 1221C defining a lumen or conduit through which nerve 1205 extends. In some examples, nerve 1205 may comprise an upper airway patency nerve such as, but not limited to, the hypoglossal nerve. While not shown for illustrative clarity, it will be understood that the cuff body 1221C may comprise a slit for removably mounting the cuff body 1221C about the nerve 1205 and/or may comprise other flanges, arms, or the like biased toward each other, to define a re-closable lumen within cuff body 1221C.

In some examples, an array of electrodes 1230A, 1230B, 1230C are mounted or supported on an inner surface of the cuff body 1221C to engage nerve 1205, and may be spaced apart from each other axially as shown or in other spaced apart configurations (e.g. circumferentially, diagonally, etc.).

As further shown in FIG. 17A, in some examples, the arrangement 1210 comprises a power/control element 1233, which may comprise at least some of substantially the same features and attributes as one of the example power/control elements, such as 160, 206, 333, 655, 865, 935, 1133, and which may be embodied as a microstimulator in some examples or as an implantable pulse generator (IPG) in some examples as previously noted.

It will be understood that in some examples a lead (such as examples shown in FIGS. 9-16B) may connect the cuff electrode 1220 to the power/control element 1233, while in some examples the cuff electrode 1220 may be in wireless communication/connection to the power/control element 1233.

In some examples, a stimulation vector ST1 may be implemented between a pair of electrodes (e.g. 1230A, 1230B) while a sensing vector SE1 may be implemented between one of the electrodes (e.g. 1230C) not used for stimulation and an electrically conductive outer portion (e.g. exposed electrode 1230D or case 1234) of the power control element 1233.

Figure 17B:
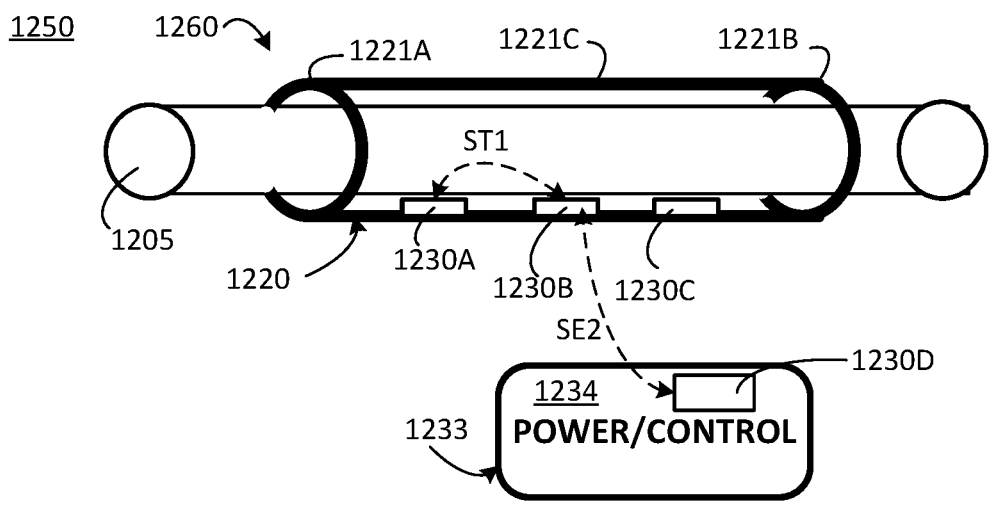

Moreover, as shown in diagram 1250 of a similar example arrangement 1260 in FIG. 17B, in some examples a stimulation vector ST1 is applied between a pair of electrodes (e.g. 1230A, 1230B) while a sensing vector SE2 is applied between one of the pair (e.g. 1230B) used for stimulation and the electrically conductive outer portion (e.g. 1234 or 1230D) of power/control element 1233. Accordingly, in this example, the electrode 1230B is shared for use in implementing a stimulation vector in some instances and in implementing a sensing vector in other instances.

In some examples, via these arrangements 1210, 1260, both sensing and stimulation may be performed simultaneously if desired.

In some examples, a single pair of electrodes (e.g. 1230A, 1230B) may be used for both stimulation and for sensing.

For instance, the stimulation vector ST1 may be applied between electrodes 1230A, 1230B for selected periods of time with predetermined suspensions of such stimulation, wherein a sensing vector SE3 may be implemented between the same electrodes 1230A, 1230B during the suspension of stimulation. In some instances, this arrangement may sometimes be referred to as a duty cycle arrangement in the sense that the same pair of electrodes (e.g. 1230A, 1230B) are being cycled to perform stimulation and sensing in an alternating manner and not being performed simultaneously. The duration of the stimulation periods and/or the duration of the suspension periods are selectable.

Figure 17C:
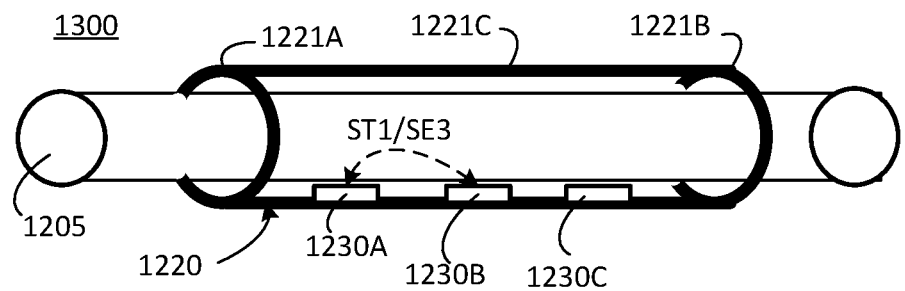
FIG. 17C is a diagram including a side view schematically representing an example device and/or example method including a cuff electrode with multiple electrodes.

In some examples, a stimulation element (e.g. 610 in at least FIGS. 9-16B) may comprise at least some of the features and attributes of the example implementations of FIGS. 17A-17C and which may be employed to sense EEG information. In some examples, respiration information also may be obtained from this sensed EEG information. In some such examples, this sensed EEG information may be sensed directly from a nerve, such as an upper airway patency nerve, which may comprise the hypoglossal nerve in some examples.

It will be understood that different example combinations of electrodes (e.g. 1230A, 1230B, 1230C) may be used to implement the above-described stimulation and sensing arrangements in FIGS. 17A-17C and/or that a greater number or fewer number of electrodes may be used in implement such stimulation and/or sensing arrangements.

Moreover, it will be understood that in some examples, a stimulation element (e.g. 610) may comprise a carrier including insulative and/or structural arrangements other than a cuff body 1221C, which may be used to support and cause electrodes (e.g. 1230A, 1230B, 1230C) to be electrically coupled relative to nerve 1205 for sensing and/or stimulation. For example, other types of carriers such as, but not limited to, a paddle carrier of a paddle-style electrode may be used to place some number of electrodes (e.g. like 1230A, 1230B, 1230C) in a sufficient proximity to nerve 1205 to enable sensing and/or stimulation of nerve 1205, and which may or may not involve actual contact with nerve 1205. It will be understood that such electrodes may be arranged in a row, which may be axial (e.g. FIGS. 17A-17C), circumferential about nerve 1205, or other arrangements (e.g. grid of 2×2, 3×3, etc.), and may comprise different numbers of electrodes.

In some examples, instead of using the cuff electrode 1220 (or other carrier-based electrode arrangement) for both sensing and stimulation, the cuff electrode 1220 (including electrodes 1230A, 1230B, 1230C) may be used solely for sensing or used solely for stimulation, and may or may not also utilize the electrically conductive outer portion (e.g. 1230D, 1234) of the power/control element 1233 in implementing such sensing or stimulation.

In some examples, the initiation, termination, duration, timing, etc. of the respective stimulation and/or sensing vectors may be controlled via a control portion (e.g. 3000 in FIG. 19A), which may be implemented in the power/control element 1233 or as otherwise described later in association with at least FIGS. 18-20.

With regard to the various examples of the present disclosure, an implant-access incision comprises a type, size and/or shape of incision adapted to permit subcutaneous implantation of the sensing element and the stimulation element. An implant-access incision in contrast to a non-implant-access incision, which may be an incision for purposes other than implanting stimulation element and/or sensing element.

With regard to the various examples of the present disclosure, in some examples, delivering stimulation to an upper airway patency nerve is to cause contraction of upper airway patency-related muscles. In some such examples, the contraction comprises a suprathreshold stimulation, which is in contrast to a subthreshold stimulation (e.g. mere tone) of such muscles. In one aspect, a suprathreshold intensity level corresponds to a stimulation energy greater than the nerve excitation threshold, such that the suprathreshold stimulation may provide for maximum upper-airway clearance (i.e. patency) and obstructive sleep apnea therapy efficacy.

In some examples, the treatment period may comprise a period of time beginning with the patient turning on the therapy device and ending with the patient turning off the device. In some examples, the treatment period may comprise a selectable, predetermined start time (e.g. 10 p.m.) and selectable, predetermined stop time (e.g. 6 a.m.). In some examples, the treatment period may comprise a period of time between an auto-detected initiation of sleep and auto-detected awake-from-sleep time. With this in mind, the treatment period corresponds to a period during which a patient is sleeping such that the stimulation of the upper airway patency-related nerve and/or central sleep apnea-related nerve is generally not perceived by the patient and so that the stimulation coincides with the patient behavior (e.g. sleeping) during which the sleep disordered breathing behavior (e.g. central or obstructive sleep apnea) would be expected to occur.

As noted elsewhere, in some examples the initiation or termination of the treatment period may be implemented automatically based on sensed EEG information, which may comprise sensed sleep state information, which in turn may comprise sleep stage information.

To avoid enabling stimulation prior to the patient falling asleep, in some examples stimulation can be enabled after expiration of a timer started by the patient (to enable therapy with a remote control), or enabled automatically via sleep stage detection. To avoid continuing stimulation after the patient wakes, stimulation can be disabled by the patient using a remote control, or automatically via sleep stage detection. Accordingly, in at least some examples, these periods may be considered to be outside of the treatment period or may be considered as a startup portion and wind down portion, respectively, of a treatment period.

In some examples, stimulation of an upper airway patency-related nerve may be performed via open loop stimulation. In some examples, the open loop stimulation may refer to performing stimulation without use of any sensory feedback of any kind relative to the stimulation.

In some examples, the open loop stimulation may refer to stimulation performed without use of sensory feedback by which timing of the stimulation (e.g. synchronization) would otherwise be determined relative to respiratory information (e.g. respiratory cycles). However, in some such examples, some sensory feedback may be utilized to determine, in general, whether the patient should receive stimulation based on a severity of sleep apnea behavior.

Conversely, in some examples and as previously described in relation to at least several examples, stimulation of an upper airway patency-related nerve may be performed via closed loop stimulation. In some examples, the closed loop stimulation may refer to performing stimulation at least partially based on sensory feedback regarding parameters of the stimulation and/or effects of the stimulation.

In some examples, the closed loop stimulation may refer to stimulation performed via use of sensory feedback by which timing of the stimulation (e.g. synchronization) is determined relative to respiratory information, such as but not limited to respiratory cycle information, which may comprise onset, offset, duration, morphology, etc. of the respiratory cycles. In some examples, the respiration information excludes (i.e. is without) tracking a respiratory volume and/or respiratory rate. In some examples, stimulation based on such synchronization may be delivered throughout a treatment period or throughout substantially the entire treatment period. In some examples, such stimulation may be delivered just during a portion or portions of a treatment period.

In some examples of "synchronization", the stimulation relative to the inspiratory phase may extend to a pre-inspiratory period and/or a post-inspiratory phase. For instance, in some such examples, a beginning of the synchronization may occur at a point in each respiratory cycle which is just prior to an onset of the inspiratory phase. In some examples, this point may be about 200 milliseconds, or 300 milliseconds prior to an onset of the inspiratory phase.

In some examples in which the stimulation is synchronous with at least a portion of the inspiratory phase, the upper airway muscles are contracted via the stimulation to ensure they are open at the time the respiratory drive controlled by the central nervous system initiates an inspiration (inhalation). In some such examples, in combination with the stimulation occurring during the inspiratory phase, example implementation of the above-noted pre-inspiratory stimulation helps to ensure that the upper airway is open before the negative pressure of inspiration within the respiratory system is applied via the diaphragm of the patient's body. In one aspect, this example arrangement may minimize the chance of constriction or collapse of the upper airway, which might otherwise occur if flow of the upper airway flow were too limited prior to the full force of inspiration occurring.

In some such examples, the stimulation of the upper airway patency-related nerve may be synchronized to occur with at least a portion of the expiratory period.

With regard to at least the methods of treating sleep apnea as previously described in association with at least FIGS. 1-17C, at least some such methods may comprise performing the delivery of stimulation to the upper airway patency-related first nerve without synchronizing such stimulation relative to a portion of a respiratory cycle. In some instances, such methods may sometimes be referred to as the previously described open loop stimulation.

In some examples, the term "without synchronizing" may refer to performing the stimulation independently of timing of a respiratory cycle. In some examples, the term "without synchronizing" may refer to performing the stimulation being aware of respiratory information but without necessarily triggering the initiation of stimulation relative to a specific portion of a respiratory cycle or without causing the stimulation to coincide with a specific portion (e.g. inspiratory phase) of respiratory cycle.

In some examples, in this context the term "without synchronizing" may refer to performing stimulation upon the detection of sleep disordered breathing behavior (e.g. obstructive sleep apnea events) but without necessarily triggering the initiation of stimulation relative to a specific portion of a respiratory cycle or without causing the stimulation to coincide with the inspiratory phase. At least some such examples may be described in Wagner et al. WO 2016/149344, STIMULATION FOR TREATING SLEEP DISORDERED BREATHING, published Sep. 22, 2016, and which is incorporated by reference herein in its entirety.

In some examples, while open loop stimulation may be performed continuously without regarding to timing of respiratory information (e.g. inspiratory phase, expiratory phase, etc.) such an example method and/or device may still comprise sensing EEG information for diagnostic data and/or to determine whether (and by how much) the continuous stimulation should be adjusted. For instance, via such EEG-sensing, it may be determined that the number of sleep disordered breathing (SDB) events are too numerous (e.g. an elevated AHI) and therefore the intensity (e.g. amplitude, frequency, pulse width, etc.) of the continuous stimulation should be increased or that the SDB events are relatively low such that the intensity of the continuous stimulation can be decreased while still providing therapeutic stimulation. It will be understood that via such EEG sensing, other SDB-related information may be determined which may be used for diagnostic purposes and/or used to determine adjustments to an intensity of stimulation, initiating stimulation, and/or terminating stimulation to treat sleep disordered breathing.

In some such examples in which closed loop stimulation may be applied using sensed respiration information, the sensing is implemented via electrically sensing brain activity, such as via electroencephalography (EEG). In some such examples, the sensed brain activity (e.g. EEG) comprises sleep stage information, which may comprise identification of specific sleep stages (e.g. S1, S2, S3, S4, REM) and/or comprise details of such sleep stages, such as the time spent in each respective stage, the number of times each stage was entered, etc. In some such examples, the sensed sleep stage information may be determined according to a power domain, frequency domain, etc.

In some examples, the sensed sleep stage information may comprise at least one parameter used to determine, track, evaluate, etc. sleep quality.

In addition, in some such examples, some sensory feedback may be utilized to determine, in general, whether the patient should receive stimulation based on a severity of sleep apnea behavior. In other words, upon sensing that a certain number of sleep apnea events are occurring, the device may implement stimulation.

Some non-limiting examples of such devices and methods to recognize and detect the various features and patterns associated with respiratory effort and flow limitations include, but are not limited to Christopherson, U.S. Pat. No. 8,938,299 Issued on Jan. 30, 2015, titled SYSTEM FOR TREATING SLEEP DISORDERED BREATHING (SDB) (formerly published as PCT Publication WO/2010/059839, titled A METHOD OF TREATING SLEEP APNEA, published on May 27, 2010); Christopherson U.S. Pat. No. 5,944,680, titled RESPIRATORY EFFORT DETECTION METHOD AND APPARATUS; and Testerman U.S. Pat. No. 5,522,862, titled METHOD AND APPARATUS FOR TREATING OBSTRUCTIVE SLEEP APNEA, each of which is hereby incorporated by reference herein in their entirety.

Moreover, in some examples various stimulation methods may be applied to treat obstructive sleep apnea, which include but are not limited to: Ni et al. U.S. 2019/0009093, published on Jan. 10, 2019, titled METHOD AND SYSTEM FOR SELECTING A STIMULATION PROTOCOL BASED ON SENSED RESPIRATORY EFFORT (previously published as WO 2013/023218, SYSTEM FOR SELECTING A STIMULATION PROTOCOL BASED ON SENSED RESPIRATORY EFFORT); Christopherson et al. U.S. Pat. No. 8,938,299, SYSTEM FOR TREATING SLEEP DISORDERED BREATHING, issued Jan. 20, 2015; and Wagner et al., U.S. 2018/0117316, STIMULATION FOR TREATING SLEEP DISORDERED BREATHING, published on May 3, 2018 (previously published as WO 2016/149344, STIMULATION FOR TREATING SLEEP DISORDERED BREATHING, on Sep. 22, 2016), each of which is hereby incorporated by reference herein in its entirety.

Figure 18:
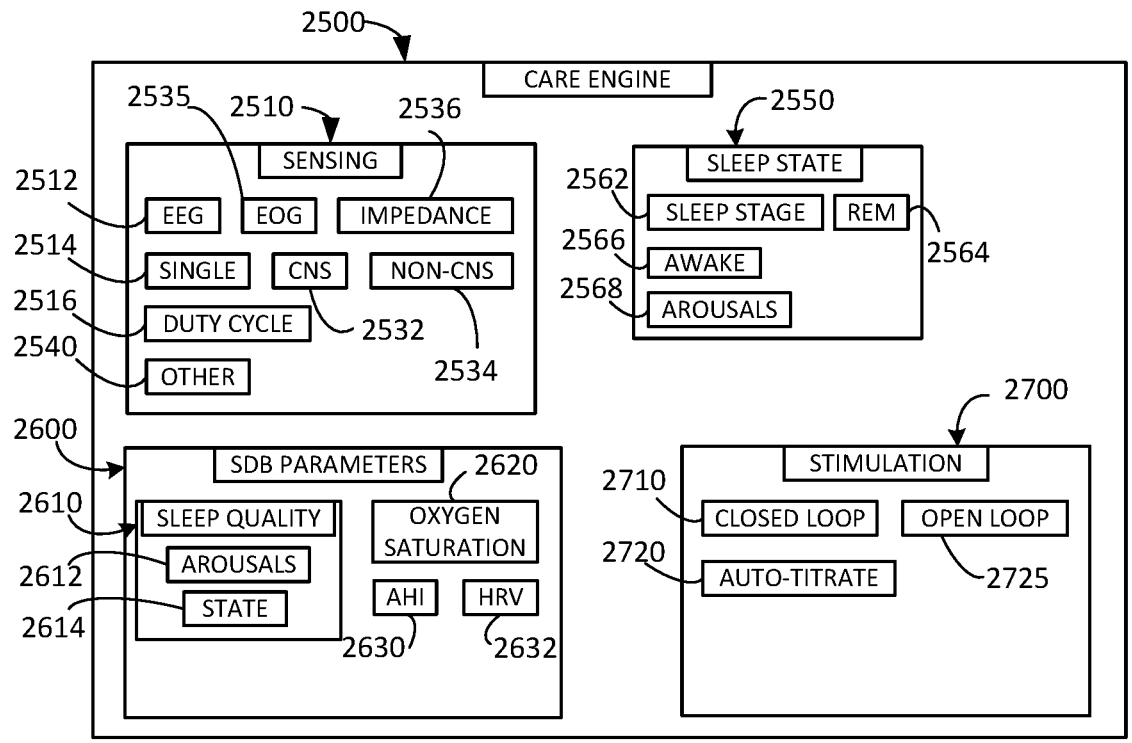
FIG. 18 is a block diagram schematically representing an example care engine.

FIG. 18 is a block diagram schematically representing an example care engine 2500. In some examples, the care engine 2500 may form part of a control portion 3000, as later described in association with at least FIG. 19A, such as but not limited to the care engine 2500 comprising at least part of the instructions 3011 and/or information 3012. In some examples, the care engine 2500 may be used to implement at least some of the various example devices and/or example methods of the present disclosure as previously described in association with FIGS. 1-17C and/or as later described in association with FIGS. 21-31. In some examples, the care engine 2500 (FIG. 18) and/or control portion 3000 (FIG. 19A) may form part of, and/or be in communication with, a pulse generator (e.g. 333, 1133) and/or a power/control element (e.g. 160, 206, 655, 865, 935) whether such elements comprise a microstimulator or other arrangement.

As shown in FIG. 18, in some examples the care engine 2500 comprises a sensing portion 2510, a sleep state portion 2550, a sleep disordered breathing (SDB) parameters 2600, and/or a stimulation portion 2700.

In some examples, the sensing portion 2510 may comprise an EEG parameter 2512 to sense EEG information, such as a single channel (2514) or multiple channels of EEG signals. In some examples, the EEG information sensed per parameter 2512 comprises sleep state information. In some such examples, the sleep state information may comprise the parameters provided in the later described sleep state portion 2550 of care engine 2500.

EEG-based sensing and/or EEG-based treatment (e.g. such as via auto-titration) according to at least some examples of the present disclosure may permit conducting sleep studies and programming remotely in a patient's home. Such examples would stand in contrast to traditional sleep studies conducted in a lab setting and use of a sleep technician. At least some such example home sleep studies may be significantly beneficial for patients with advanced diseases states: mixed mode sleep apnea, Narcolepsy, epilepsy, and/or Parkinson's disease. In addition, the EEG-based sensing can be used to detect additional diagnostic data associated with these advanced disease states.

In some such examples of EEG-based sensing and/or EEG-based treatment, the sensing and/or treatment may be employed to monitor respiration of the patient. However, in other such examples of EEG-based sensing and/or EEG-based treatment, the sensing and/or treatment may be employed without monitoring respiration of the patient.

There may be a minor subset of patients who can hear stimulation. In some examples, the use of EEG sensing may be able to identify the mechanism by which the patient can hear the stimulation, and then the stimulation intensity level can be adjusted to ameliorate the patient's hearing of stimulation. In some such examples, a cochlear implant may act as a pulse generator to deliver the stimulation (via a stimulation lead) and to measure sleep information. In some such examples, the cochlear implant can communicate wirelessly with a sleep disordered breathing (SDB) stimulator to measure impedances and establish additional sensing vectors.

As further shown in FIG. 18, in some examples the sensing portion 2510 comprises a duty cycle parameter 2516 to control the timing (e.g. duration, frequency, etc.) by which a sensing element is to sense physiologic information, such as but not limited to EEG information. In particular, because sensing EEG information may be somewhat power intensive, the sensing portion 2510 may perform the sensing at least a portion of a treatment period according to a duty cycle instead of continuously sensing the EEG information. For instance, the EEG information may be sensed for just a portion each stage each night or may be sensed just on some nights instead of every night. However, it will be understood that in some instances, continuous sensing of the EEG information may be performed throughout an entire treatment period or during select portions of a treatment period.

In some examples, such sensed EEG information may be transmitted to an external EEG monitor that communicates with an implanted sensing element (and/or monitor, pulse generator) to collect data obtained by the implanted components.

In some examples, the duty cycle parameter 2516 may be employed to control cycling between sensing and stimulation when a set of electrodes (e.g. 1230A, 1230B, 1230C in FIGS. 17A-17C) may be used for both stimulation and sensing.

In some examples, the EEG information 2512 may be processed at least partially in an implanted component (e.g. monitor, pulse generator, and/or sensing element) in order to lessen or avoid the power and time load that might otherwise occur in uploading large data sets, with the remainder of the processing being performed externally as noted above. In some such examples, artificial intelligence and/or machine learning may be implemented to reduce data processing/power demands, and in some examples is implemented externally of the patient. In some examples, the implanted components (e.g. monitor, pulse generator) may be trained to simplify the type of data to be tracked, uploaded, etc. as well as to optimize the manner of tracking, etc.

In some examples, the EEG information (2512) may comprise sleep state information, and as further shown in FIG. 18, the care engine 2500 may comprise a sleep state portion 2550 to sense and/or track sleep state information obtained via the EEG information parameter 2512. In some examples, the sleep state portion 2550 may identify and/or track start of sleep and/or end of sleep (e.g. awake state), as well as identify and/or track sleep stages once the patient is asleep. Accordingly, in some examples, the sleep state portion 2550 comprises sleep stage parameter 2562 to identify and/or track various sleep stages (e.g. S1, S2, S3, S4, REM) of the patient during a treatment portion or during longer periods of time. It will be understood that other nomenclature (e.g. N1, N2, N3) may be used instead of S1, S2, S3, S4 to refer to various sleep stages. The sleep state portion 2550 also may comprise, in some examples, a separate rapid eye movement (REM) parameter 2564 to sense and/or track REM information in association with various aspects of sleep disordered breathing (SDB) care, as further described below and throughout various examples of the present disclosure. In some examples, the REM parameter 2564 may form part of, or be used with, the sleep stage parameter 2562.

In some examples, the sleep state portion 2550 may comprise an awake parameter 2566 to sense and/or track an awake state of the patient. An awake state of a patient may be indicative of general non-sleep periods (e.g. day time) and/or of interrupted sleep events, such as arousals (per parameter 2568) associated with sleep disordered breathing (SDB) events in which a patient is awakened due to sleep apnea, such as but not limited to obstructive sleep apnea, central sleep apnea, and/or hypopneas.

In some such examples and as previously described, the sleep state information (per sleep state portion 2550) may be used to sense, track, and/or diagnose sleep disordered breathing (SDB) behavior. In some such examples and as previously described, the sleep state information may be used in a closed-loop manner to initiate, terminate, and/or adjust stimulation therapy to treat sleep disordered breathing (SDB) behavior to enhance device efficacy. For instance, in some examples via sensing an awake state 2566 (via sleep state portion 2550), stimulation therapy may be terminated automatically. In some examples, via sensing commencement of particular sleep stages (2562), stimulation therapy may be initiated automatically. In some examples, the intensity of stimulation therapy may be adjusted and implemented according to a particular sleep stage and/or particular characteristics within a sleep stage. In some examples, a lower stimulation intensity level may be implemented upon detecting a REM sleep stage. In some examples, stimulation intensity may be decreased in some sleep stages to conserve power and battery life.

In some examples, in cooperation with at least sleep stage parameter 2562 of care engine 2500, delivery of a stimulation signal may be toggled among different predetermined intensity levels for each different sleep stage (e.g. S1, S2, S3, S4, REM). For instance, a first stimulation intensity level may be delivered for a first sleep stage (e.g. S1) while a second, different stimulation intensity level may be delivered for a second sleep stage (e.g. S2), and so on for the respective third and fourth sleep stages. In some such examples, the same predetermined stimulation intensity level may be delivered for at least two consecutive different sleep stages (e.g. S2 and S3) or for at least two different non-consecutive sleep stages (e.g. S2 and S4). It will be understood that in some such examples, the determination by care engine 2500 of which predetermined stimulation intensity level is to be delivered to the patient is to be made solely according the sleep stage of the patient, such that a change among different predetermined stimulation intensity levels may be implemented without sensing an apnea severity index (AHI), may be implemented without on-going sensing of sleep quality, etc.

In some such examples, via at least sleep stage parameter 2562 and stimulation portion 2700, the care engine 2500 may switch (e.g. automatically) among the different stimulation intensity levels regardless of the frequency or number of times that a particular sleep stage occurs in a treatment period (e.g. a single night of sleep) and/or regardless of how long each sleep stage occurs.

However, in some examples, via sleep stage parameter 2562 and/or stimulation portion 2700, the care engine 2500 may delay switching from one intensity level (for a particular sleep stage) to a second, different intensity level for a different sleep stage until the second, different sleep stage lasts up to and/or beyond a predetermined threshold. It will be understood that in this context the term "second" may refer to any one of the traditionally numbered sleep stages (e.g. S1, S2, S3, S4, REM) and does not strictly refer to sleep stage S2. The predetermined threshold may be programmed by a clinician or operate according to a default value.

In some such examples, a different stimulation intensity level may be implemented by changing at least one of an amplitude, frequency, pulse width, etc. of the stimulation signal.

In some such examples, the sleep state information may be indicative of sleep quality, which may be sensed and/or tracked per sleep quality portion 2610, as further described in some later examples. Moreover, this sleep state information is further described later in association with at least stimulation portion 2700 of care engine 2500.

In some examples, the sensing portion 2510 comprises a central nervous system (CNS) parameter 2532 which corresponds to the sensing portion 2510 sensing (via a sensing element) central nervous system information via the EEG signal (per parameter 2512). However, it will be understood that EEG information comprises a portion of the CNS information which may be sensed via a sensing element. In some examples, the CNS information comprises solely that CNS information which is sensed in the head-and-neck region of the patient.

In some examples, the sensing portion 2510 comprises a non-central nervous system (non-CNS) parameter 2534, which corresponds to the sensing portion 2510 sensing (via a sensing element) non-CNS information.

In some examples, non-CNS information obtainable from a head-and-neck portion also may be used to inform and/or drive care, with such non-CNS information being used alone and/or in combination with CNS information. For example, in some instances the sensing portion 2510 may comprise an electro-oculogram (EOG) parameter 2535, which relates to sensing and/or tracking eye movement, eye position, etc. In some such examples, the sensing element may comprise an optical sensor.

In some examples, this EOG information may be used as part of determining and/or confirming sleep state information, among other CNS information (2532) which may be used to sense, diagnose, and/or treat sleep disordered breathing (SDB) behavior. For instance, in some such examples, this EOG information may comprise detection and/or tracking of rapid eye movement (REM) per parameter 2564 during sleep, which in turn may be used in differentiating between an awake state, REM state, and/or other sleep states, including various sleep stages. In some examples, the absence of REM sleep as tracked per parameter 2564 may be indicative of poor sleep quality because the patient is not getting to REM sleep. Such information may be used to adjust the therapy by increasing stimulation intensity (e.g. frequency, amplitude, and/or pulse width, treatment period, etc.) in an attempt to reduce the number of SDB events, arousals, etc. so the patient can get more REM sleep. Conversely, detecting the occurrence of REM sleep (per parameter 2564) for a particular patient may be indicative that stimulation therapy is effective (e.g. sufficient stimulation intensity). In some such examples, this REM information (2564) may be used along with other sleep state information and/or other SDB-related physiologic information to evaluate sleep quality, which in turn may be used to automatically titrate (e.g. increase or decrease) stimulation therapy to treat sleep disordered breathing (SDB).

In some examples, a sensing element for obtaining EOG information may be implanted in the head-and-neck portion, such as adjacent the eyes, eye muscles, and/or eye nerves, etc. In some examples, the sensing element may communicate the EOG information wirelessly, or via an implanted lead, to a control element (e.g. monitor, pulse generator, and the like) implanted within the head-and-neck region. In some such examples, the sensing element may comprise an electrode implanted near one or both eyes of the patient. In some examples, the EOG sensing element may comprise one of the example sensing elements as previously described in association with FIGS. 1-17C.

However, in some examples, the EOG information may be obtained via external sensing elements which are worn on the head or which may observe the eye movement, position, etc. such as via a mobile phone, monitoring station within proximity to the patient, and the like. Such externally-obtained EOG information may be communicated wirelessly to an implanted monitor, pulse generator and the like which controls sensing elements and/or stimulation elements implanted within the patient's body.

In some examples, the CNS information and/or the non-CNS information obtained in the head-and-neck region may be obtained via at least some of the examples of the present disclosure for implantation and/or other implementation of sensing, monitoring, stimulation, delivery, etc.

In some examples, the sensing portion 2510 comprises an impedance parameter 2536 to sense and/or track sensing of impedance within the patient's body, which may be used to sense respiratory information, and/or other information in association with sleep disordered breathing (SDB) care.

In some examples, the sensing portion 2510 comprises an other parameter 2540 to sense and/or track sensed information other than the previously described information sensed via the sensing portion 2510. For instance, in some examples, sensing EEG-based physiologic information and/or sensing other head-and-neck-based (e.g. non-EEG) physiologic information may be used to treat sleep disordered breathing (SDB) in patients which also exhibit advanced disease states, such as multiple type sleep apnea, narcolepsy, epilepsy, Parkinson's, in which the sensed physiologic information may sense or track additional diagnostic data regarding such other diseases.

In some examples, the other parameter 2540 may sense and/or track sensed information regarding a posture of the patient, which may be indicative of an awake or sleep state of the patient. In some such examples, a sensing element of the device (e.g. FIGS. 1-17C) may comprise an accelerometer. In some such examples, the sensing element may form a portion of pulse generator or microstimulator. Alternatively, in some examples the sensed posture information may be obtained from a sensor located elsewhere in or on the body and which is communicated to a control element (e.g. monitor or pulse generator) of an example device. In some examples, a stimulation therapy level may be determined and/or automatically adjusted depending upon a particular posture or changes in posture.

In some examples, the other parameter 2540 may utilize sensed EEG information (including sleep state information) to detect and differentiate central sleep apnea and obstructive sleep apnea from each other. In some such examples, this differentiation may facilitate recognition of and/or treatment of multiple type apnea.

In some examples, the other parameter 2540 may comprise sensing of heart rate information, with the sensing element comprising: an electrocardiogram sensing element in the torso region; an EEG sensing element(s); and/or an accelerometer, etc.

As further shown in FIG. 18, in some examples the care engine 2500 comprises a SDB parameters portion 2600 which senses and/or tracks parameters particularly associated with sleep disordered breathing (SDB) care. For instance, in some examples, the SDB parameters portion 2600 comprises a sleep quality portion 2610 to sense and/or track sleep quality of the patient in particular relation to the sleep disordered breathing behavior of the patient. Accordingly, in some examples the sleep quality portion 2610 comprises an arousals parameter 2612 to sense and/or track arousals caused by sleep disordered breathing (SDB) events with the number, frequency, duration, etc. of such arousals being indicative of sleep quality (or lack thereof).

In some examples, the sleep quality portion 2610 comprises a state parameter 2614 to sense and/or track the occurrence of various sleep states (including sleep stages) of a patient during a treatment period or over a longer period of time. In some such examples, the state parameter 2614 may cooperate with, form part of, and/or comprise at least some of substantially the same features and attributes as sleep state portion 2550 of care engine 2500.

As further shown in FIG. 18, in some examples, the SDB parameters portion 2600 comprises an oxygen saturation parameter 2620 to sense and/or track a patient's oxygen saturation (e.g. during a treatment period) to at least partially determine sleep quality for the patient. In some examples, this parameter 2620 may be referred to as a blood oxygen desaturation parameter. In some examples, oxygen saturation information is sensed throughout each of the different sleep stages experienced by a patient, with such sensed oxygen saturation information being at least partially indicative of a degree of sleep disordered breathing (SDB) behavior. In some examples, the oxygen saturation information is obtained via a sensing element, such as optical sensing element, which may be located in a lead portion associated with the implantable elements (e.g. sensing, stimulation, etc.). In some examples, the optical sensing element may be located in a connector portion by which lead portions are electrically and mechanically connected to a pulse generator (and/or monitoring device). In some such examples, the optical sensing element may be implemented as an external sensor, such as but not limited to a finger-mountable sensor or other body-mountable sensor. In some such examples, the optical sensing of oxygen saturation information may comprise pulse oximetry sensing.

In some examples, the SDB parameters portion 2600 comprises an AHI parameter 2630 to sense and/or track apnea-hypopnea index (AHI) information, which may be indicative of the patient's sleep quality. In some examples, AHI information is sensed throughout each of the different sleep stages experienced by a patient, with such sensed AHI information being at least partially indicative of a degree of sleep disordered breathing (SDB) behavior. In some examples, the AHI information is obtained via a sensing element, such as an EEG sensing arrangement, which may be implemented in via the example implementations as described in various examples of the present disclosure. In some examples, AHI information may be sensed via a sensing element, such as an accelerometer located in either the torso or chin/neck region with the sensing element locatable and implemented as described in various examples of the present disclosure. In some examples, both EEG-based sensing and accelerometer-based sensing may be employed to sense and/or track AHI information.

In some examples, the SDB parameters portion 2600 comprises a cardiac parameter 2632 to sense and/or track cardiac information, which may be indicative of the patient's sleep quality and which may be used alone or in conjunction with REM sleep information, oxygen saturation information, etc. to determine sleep quality. In some such examples, the cardiac information sensed and/or tracked via parameter 2632 may comprise heart rate information. In some such examples, the cardiac information may comprise heart rate variability (HRV) information.

As further shown in FIG. 18, in some examples care engine 2500 comprises a stimulation portion 2700 to control stimulation of target tissues, such as but not limited to an upper airway patency nerve, to treat sleep disordered breathing (SDB) behavior. In some examples, the stimulation portion 2700 comprises a closed loop parameter 2710 to deliver stimulation therapy in a closed loop manner such that the delivered stimulation is in response to and/or based on sensed patient physiologic information.

This sensed physiologic information may be used to determine whether stimulation should be performed. For example, the sensed physiologic information may comprise sleep quality in which poor sleep quality may indicate initiating stimulation therapy or increasing stimulation therapy intensity, while better sleep quality may indicate terminating stimulation therapy or reducing stimulation therapy intensity. In some such examples, such adjustments may be triggered according to a patient's particular sleep stages in which greater stimulation therapy intensity is automatically applied in certain sleep stages and/or in which lesser stimulation therapy intensity is automatically applied in other sleep stages. As previously noted, such adjustments may be implemented via adjusting an amplitude, frequency, and/or pulse width, etc. of a stimulation signal.

In some examples, the closed loop parameter 2710 may be implemented as using the sensed information to control the particular timing of the stimulation according to respiratory information, in which the stimulation pulses are triggered by or synchronized with specific portions (e.g. inspiratory phase) of the patient's respiratory cycle(s). In some such examples and as previously described, this respiratory information may be determined via sensed EEG information (2512).

As further shown in FIG. 18, in some examples the stimulation portion 2700 comprises an open loop parameter 2725 by which stimulation therapy is applied without a feedback loop of sensed physiologic information. In some such examples, in an open loop mode the stimulation therapy is applied during a treatment period without (e.g. independent of) information sensed regarding the patient's sleep quality, sleep state, AHI, etc. In some such examples, in an open loop mode the stimulation therapy is applied during a treatment period without (i.e. independent of) particular knowledge of the patient's respiratory cycle information.

As further shown in FIG. 18, in some examples the stimulation portion 2700 comprises an auto-titration parameter 2720 by which an intensity of stimulation therapy can be automatically titrated (i.e. adjusted) to be more intense (e.g. higher amplitude, greater frequency, and/or greater pulse width) or to be less intense within a treatment period.

In some such examples and as previously described, such auto-titration may be implemented based on sleep quality and/or sleep state information, which may be obtained via sensed EEG information, in some examples. It will be understood that such examples may be employed with synchronizing stimulation to sensed respiratory information (i.e. closed loop stimulation) or may be employed without synchronizing stimulation to sensed respiratory information (i.e. open loop stimulation).

In some examples, via the auto-titration parameter 2720 and via the sensed EEG information (including sleep state information), an in-home sleep study may be performed in which the example device and/or example method may forego manual titration based on observations of a technician.

Figure 19A:
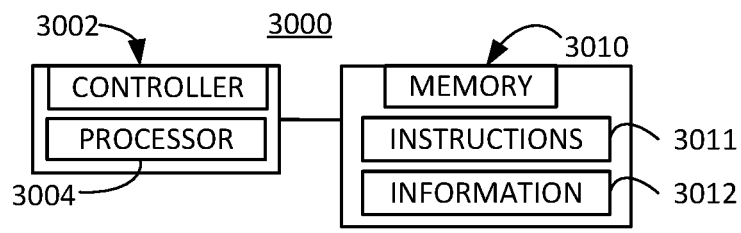
FIGS. 19A and 19B are each a block diagram schematically representing an example control portion.

FIG. 19A is a block diagram schematically representing an example control portion 3000. In some examples, control portion 3000 provides one example implementation of a control portion forming a part of, implementing, and/or generally managing stimulation elements, power/control elements (e.g. pulse generators, microstimulators), sensors, and related elements, devices, user interfaces, instructions, information, engines, elements, functions, actions, and/or methods, as described throughout examples of the present disclosure in association with FIGS. 1-18 and 19B-31.

In some examples, control portion 3000 includes a controller 3002 and a memory 3010. In general terms, controller 3002 of control portion 3000 comprises at least one processor 3004 and associated memories. The controller 3002 is electrically couplable to, and in communication with, memory 3010 to generate control signals to direct operation of at least some of the stimulation elements, power/control elements (e.g. pulse generators, microstimulators) sensors, and related elements, devices, user interfaces, instructions, information, engines, elements, functions, actions, and/or methods, as described throughout examples of the present disclosure. In some examples, these generated control signals include, but are not limited to, employing instructions 3011 and/or information 3012 stored in memory 3010 to at least direct and manage treatment of sleep disordered breathing such as obstructive sleep apnea, hypopnea, and/or central sleep apnea, sensing physiologic information including but not limited to central nervous system (CNS) information (including brain state, sleep stage, EEG, etc.), respiratory information, heart rate, and/or monitoring sleep disordered breathing, etc. as described throughout the examples of the present disclosure in association with FIGS. 1-18 and 19B-31. In some instances, the controller 3002 or control portion 3000 may sometimes be referred to as being programmed to perform the above-identified actions, functions, etc. In some examples, at least some of the stored instructions 3011 are implemented as, or may be referred to as, a care engine, a sensing engine, monitoring engine, and/or treatment engine. In some examples, at least some of the stored instructions 3011 and/or information 3012 may form at least part of, and/or, may be referred to as a care engine (e.g. 2500 in FIG. 18), sensing engine, monitoring engine, and/or treatment engine.

In response to or based upon commands received via a user interface (e.g. user interface 3020 in FIG. 20) and/or via machine readable instructions, controller 3002 generates control signals as described above in accordance with at least some of the examples of the present disclosure. In some examples, controller 3002 is embodied in a general purpose computing device while in some examples, controller 3002 is incorporated into or associated with at least some of the stimulation elements, power/control elements (e.g. pulse generators, microstimulators), sensors, and related elements, devices, user interfaces, instructions, information, engines, functions, actions, and/or method, etc. as described throughout examples of the present disclosure.

For purposes of this application, in reference to the controller 3002, the term "processor" shall mean a presently developed or future developed processor (or processing resources) that executes machine readable instructions contained in a memory. In some examples, execution of the machine readable instructions, such as those provided via memory 3010 of control portion 3000 cause the processor to perform the above-identified actions, such as operating controller 3002 to implement the sensing, monitoring, treatment, etc. as generally described in (or consistent with) at least some examples of the present disclosure. The machine readable instructions may be loaded in a random access memory (RAM) for execution by the processor from their stored location in a read only memory (ROM), a mass storage device, or some other persistent storage (e.g., non-transitory tangible medium or non-volatile tangible medium), as represented by memory 3010. In some examples, the machine readable instructions may comprise a sequence of instructions, a processor-executable machine learning model, or the like. In some examples, memory 3010 comprises a computer readable tangible medium providing non-volatile storage of the machine readable instructions executable by a process of controller 3002. In some examples, the computer readable tangible medium may sometimes be referred to as, and/or comprise at least a portion of, a computer program product. In other examples, hard wired circuitry may be used in place of or in combination with machine readable instructions to implement the functions described. For example, controller 3002 may be embodied as part of at least one application-specific integrated circuit (ASIC), at least one field-programmable gate array (FPGA), and/or the like. In at least some examples, the controller 3002 is not limited to any specific combination of hardware circuitry and machine readable instructions, nor limited to any particular source for the machine readable instructions executed by the controller 3002.

In some examples, control portion 3000 may be entirely implemented within or by a stand-alone device.

In some examples, the control portion 3000 may be partially implemented in one of the sensing devices, monitoring devices, stimulation devices, apnea treatment devices (or portions thereof), etc. and partially implemented in a computing resource separate from, and independent of, the apnea treatment devices (or portions thereof) but in communication with the apnea treatment devices (or portions thereof). For instance, in some examples control portion 3000 may be implemented via a server accessible via the cloud and/or other network pathways. In some examples, the control portion 3000 may be distributed or apportioned among multiple devices or resources such as among a server, an apnea treatment device (or portion thereof), and/or a user interface.

Figures 19B, 20:
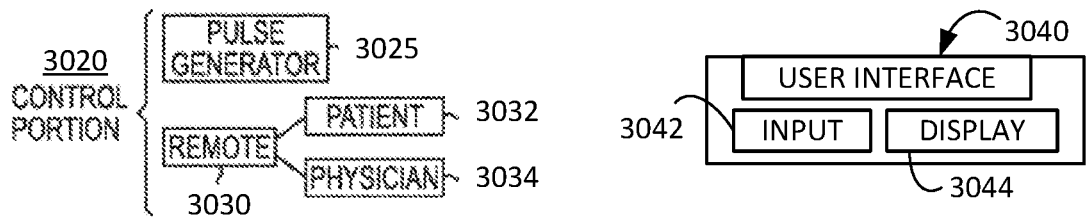
FIG. 20 is a block diagram schematically representing an example user interface.

In some examples, control portion 3000 includes, and/or is in communication with, a user interface 3020 as shown in FIG. 20.

FIG. 19B is a diagram schematically illustrating at least some example implementations of a control portion 3020 by which the control portion 3000 (FIG. 19A) can be implemented, according to one example of the present disclosure. In some examples, control portion 3020 is entirely implemented within or by an IPG assembly 3025, which has at least some of substantially the same features and attributes as a pulse generator (e.g. power/control element, microstimulator) as previously described throughout the present disclosure. In some examples, control portion 3020 is entirely implemented within or by a remote control 3030 (e.g. a programmer) external to the patient's body, such as a patient control 3032 and/or a physician control 3034. In some examples, the control portion 3000 is partially implemented in the IPG assembly 3025 and partially implemented in the remote control 3030 (at least one of patient control 3032 and physician control 3034).

FIG. 20 is a block diagram schematically representing user interface 3040, according to one example of the present disclosure. In some examples, user interface 3040 forms part or and/or is accessible via a device external to the patient and by which the therapy system may be at least partially controlled and/or monitored. The external device which hosts user interface 3040 may be a patient remote (e.g. 3032 in FIG. 19B), a physician remote (e.g. 3034 in FIG. 19B) and/or a clinician portal. In some examples, user interface 3040 comprises a user interface or other display that provides for the simultaneous display, activation, and/or operation of at least some of the stimulation elements, power/control elements (e.g. pulse generators, microstimulators), sensors, and related elements, devices, user interfaces, instructions, information, engines, functions, actions, and/or method, etc., as described in association with FIGS. 1-31. In some examples, at least some portions or aspects of the user interface 3040 are provided via a graphical user interface (GUI), and may comprise a display 3044 and input 3042.

Each of FIGS. 21-31 schematically represent at least some of substantially the same features and attributes as the example devices and/or example methods, as previously described in association with at least FIGS. 1-20, and may comprise an example implementation of at least some of those previously described examples.

Figure 21:
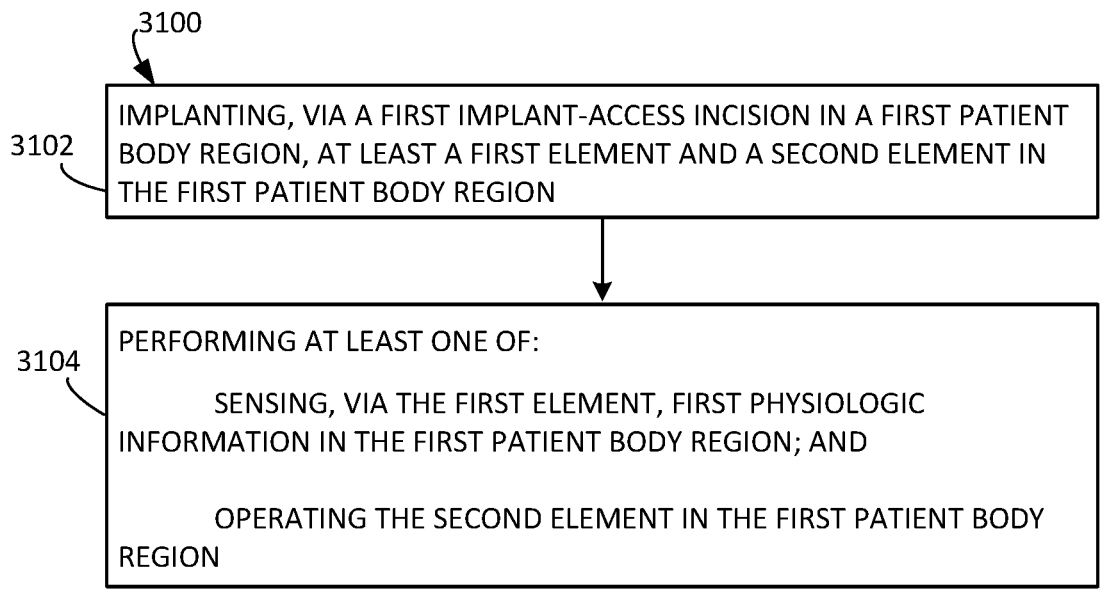
FIG. 21 is a flow diagram schematically representing an example method including sensing via a first element and/or operating a second element.

As shown at 3102 in FIG. 21, in some examples method 3100 comprises implanting, a first implant-access incision in a first patient body region, at least a first element and a second element in the first patient body region. As shown at 3104 in FIG. 21, method 3100 comprises performing at least one of: sensing, via the first element, first physiologic information in the first patient body region; and operating the second element in the first patient body region.

Figure 22:
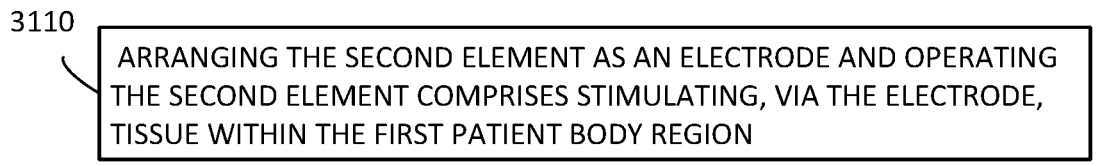
FIG. 22 is a block diagram schematically representing an example method including stimulating tissue.
Figure 23:
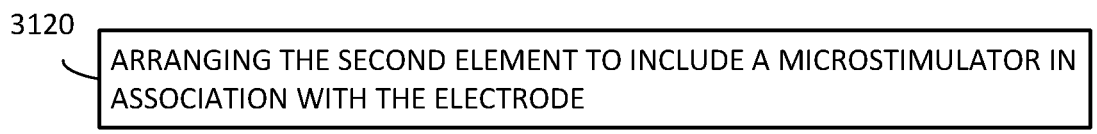
FIG. 23 is a block diagram schematically representing an example method including arranging a second element as a microstimulator.

As shown at 3110 in FIG. 22, in some examples method 3100 further comprises arranging the second element as an electrode and operating the second element comprises stimulating, via the electrode, tissue within the first patient body region. As shown at 3120 in FIG. 23, in some such examples the method may comprise arranging the second element to include a microstimulator in association with the stimulation electrode.

Figure 24:
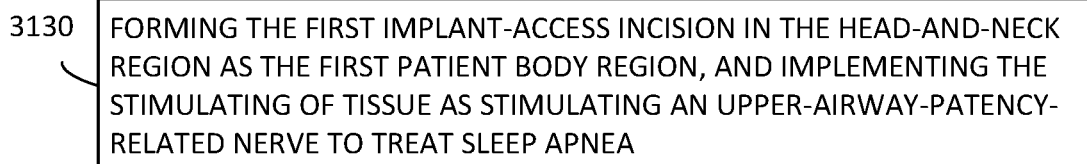
FIG. 24 is block diagram schematically representing an example method including forming an implant-access incision in a head-and-neck region and stimulating an upper-airway-patency-related nerve.

As shown at 3130 in FIG. 24, in some examples method 3100 comprises forming the first implant-access incision in the head-and-neck region as the first patient body region, and implementing the stimulating of tissue as stimulating an upper airway patency nerve to treat sleep apnea.

As shown at 3200 in FIG. 25, in some examples method 3100 may comprise arranging the first element to sense EEG information. As shown at 3220 in FIG. 26, in some examples method 3100 may comprise operating the second element, based on the sensed EEG information, to stimulate an upper airway patency nerve to treat sleep disordered breathing (SDB).

As shown at 3240 in FIG. 27, in some examples method 3100 may comprise sensing the EEG information to determine sleep state information and determining SDB care information based on the determined sleep state information. In some examples, such sleep state information comprises, but is not limited to, sleep stage information.

As shown in FIG. 28, in some examples method 3260 may comprise sensing the EEG information to determine sleep state information and determining SDB care information based on the determined sleep state information.

As shown at 3310 in FIG. 29, in some examples a method 3300 may comprise implanting elements of a sleep disordered breathing (SDB) care device solely within a head-and-neck region. As shown at 3320, method 3300 may comprise sensing, via a first implanted electrode of the SDB care device, EEG information including at least sleep state information. As shown at 3340, method 3300 may comprise stimulating, via a second implanted electrode of the SDB care device, an upper airway patency nerve to treat sleep disordered breathing.

As shown at 3350 in FIG. 30, in some examples method 3350 may comprise performing the stimulating in a closed-loop manner based on the sensed EEG information.

As shown at 3360 in FIG. 31, in some examples method 3360 may comprise arranging the second element (e.g. 120) in association with a microstimulator of the SDB care device. For example, as previously described in some examples, the second element may comprise an electrode(s) which is connected to but extends from (via a lead) a microstimulator or may comprise an electrode(s) which is incorporated into or onto a surface of a housing of a microstimulator, or variations thereof. In some such examples, such second element may comprise a stimulation element and/or a sensing element.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein.

The invention claimed is:

1. A method of treating obstructive sleep apnea comprising:
   chronically subdermally implanting, via a first implant-access incision, at least a first element and a second element in a head-and-neck region; and
   sensing, via the first element, first physiologic information in the head-and-neck region via sensing EEG information, which comprises respiratory information, wherein the respiratory information comprises respiratory cycle information including inspiratory phase information and expiratory phase information, and wherein the EEG information comprises the sole source of the respiratory information; and
   applying stimulation via the second element to an upper airway patency-related nerve in the head-and-neck region, including synchronizing the applied stimulation in a closed loop manner to the sensed respiratory phase information including inspiratory phase information,
      wherein the second element comprises a stimulation electrode, a pulse generator, and a lead extending outwardly from a housing of the pulse generator to support the stimulation electrode in a spaced apart position relative to the housing.

2. The method of claim 1, comprising:
   arranging the first element to be electrically connected to the pulse generator and spaced apart from the pulse generator; and
   performing the sensing of the first physiologic information on tissue interposed between the first element and an exposed sensing portion on the housing of the pulse generator.

3. The method of claim 1, comprising at least one of:
   determining sleep stage information based on the sensed EEG information and adjusting an intensity of the stimulation based on the determined sleep stage information; or
   identifying, via the EEG information, sleep stage information and using the identified sleep stage information, identifying and tracking sleep disordered breathing (SDB) events throughout different sleep stages.

4. The method of claim 3, comprising:
   identifying the SDB events according to at least one of an apnea-hypopnea index (AHI) and an oxygen saturation level.

5. The method of claim 1, and further comprising:
   determining, via the sensed EEG information, at least sleep state information and the respiratory information; and
   based on at least the sleep state information and the respiratory information, performing at least one of:
      initiating stimulation;
      adjusting stimulation; and
      terminating stimulation.

6. The method of claim 5, comprising at least one of:
wherein the adjusting stimulation comprises automatically increasing or decreasing an intensity of stimulation relative to an efficacy threshold, the efficacy threshold comprising at least one of AHI and SaO2; and
wherein the adjusting stimulation comprises automatically selecting an intensity of stimulation from among a plurality of different stimulation intensities, wherein each different stimulation intensity corresponds to one sleep stage of a plurality of sleep stages.

7. A method of treating obstructive sleep apnea comprising:
chronically subdermally implanting a single electrode-carrier arrangement, via a first implant-access incision, in a first final implant location in a mandible-neck region of the head-and-neck region external to a cranium portion of the head-and-neck region, wherein the first single electrode-carrier arrangement comprises an array of electrodes in which at least a pair of the electrodes comprise stimulation electrodes and at least one electrode of the array of electrodes comprises a sensing electrode; and
sensing, via the single electrode-carrier arrangement, first physiologic information in the head-and-neck region via sensing EEG information, which comprises respiratory information, wherein the respiratory information comprises respiratory cycle information including inspiratory phase information and expiratory phase information, wherein the EEG information comprises the sole source of the respiratory information; and
applying stimulation via the stimulation electrodes to an upper airway patency-related nerve adjacent the first final implant location in the head-and-neck region, including synchronizing the applied stimulation in a closed loop manner to the sensed respiratory phase information including the inspiratory phase information,
wherein the single electrode-carrier arrangement is supported on a lead extending outwardly from a housing of a pulse generator to support the single electrode-carrier arrangement in a spaced apart position relative to the housing.

8. The method of claim 7, comprising:
obtaining sleep stage information from the sensed EEG information and determining a parameter of the stimulation based on the obtained sleep stage information.

9. The method of claim 7, wherein the single electrode-carrier arrangement comprises a cuff electrode.

10. The method of claim 7, wherein the at least one electrode of the array of electrodes acting the sensing electrode also comprises a respective one of the stimulation electrodes.

11. The method of claim 10, wherein the sensing comprises sensing via a first sensing vector between the pair of electrodes comprising stimulation electrodes.

12. The method of claim 11, wherein the sensing comprises sensing via a second sensing vector between the at least one electrode acting as the sensing element and a power/control element spaced apart from the single electrode-carrier arrangement.

13. The method of claim 7, wherein the single electrode-carrier arrangement comprises a paddle electrode.

14. The method of claim 7, wherein the sensing of the EEG information via the single electrode-carrier arrangement comprises sensing the EEG information as single EEG channel.

15. The method of claim 7, comprising at least one of:
determining sleep stage information based on the sensed EEG information and adjusting an intensity of the stimulation based on the determined sleep stage information; or
identifying, via the EEG information, sleep stage information and using the identified sleep stage information, identifying and tracking sleep disordered breathing (SDB) events throughout different sleep stages.

16. The method of claim 7, comprising:
identifying the SDB events according to at least one of an apnea-hypopnea index (AHI) and an oxygen saturation level.

17. The method of claim 7, and further comprising:
determining, via the sensed EEG information, at least sleep state information and the respiratory information; and
based on at least the sleep state information and the respiratory information, performing at least one of:
initiating stimulation;
adjusting stimulation; and
terminating stimulation.

18. The method of claim 17, comprising at least one of:
wherein the adjusting stimulation comprises automatically increasing or decreasing an intensity of stimulation relative to an efficacy threshold, the efficacy threshold comprising at least one of AHI and SaO2; and
wherein adjusting stimulation comprises automatically selecting an intensity of stimulation from among a plurality of different stimulation intensities, wherein each different stimulation intensity corresponds to one sleep stage of a plurality of sleep stages.

* * * * *

UNITED STATES PATENT AND TRADEMARK OFFICE
CERTIFICATE OF CORRECTION

| | |
|---|---|
| PATENT NO. | : 12,311,179 B2 |
| APPLICATION NO. | : 16/977677 |
| DATED | : May 27, 2025 |
| INVENTOR(S) | : Kevin Verzal et al. |

It is certified that error appears in the above-identified patent and that said Letters Patent is hereby corrected as shown below:

In the Specification

Column 33, Line 8, delete "saturation" and insert in place thereof --saturation (SaO2)--.

In the Claims

Claim 7, Line 6, delete "region of the head-and-neck" and insert in place thereof --region of a head-and-neck--.

Claim 7, Line 8, delete "first single" and insert in place thereof --single--.

Claim 10, Line 2, delete "electrodes acting the" and insert in place thereof --electrodes comprising the--.

Claim 12, Line 3, delete "electrode acting as the sensing element" and insert in place thereof --electrode comprising the sensing electrode--.

Claim 14, Line 3, delete "as single" and insert in place thereof --as a single--.

Signed and Sealed this
Eighth Day of July, 2025

Coke Morgan Stewart
*Acting Director of the United States Patent and Trademark Office*